United States Patent [19]
Hardy et al.

[11] Patent Number: 5,354,314
[45] Date of Patent: * Oct. 11, 1994

[54] THREE-DIMENSIONAL BEAM LOCALIZATION APPARATUS AND MICROSCOPE FOR STEREOTACTIC DIAGNOSES OR SURGERY MOUNTED ON ROBOTIC TYPE ARM

[75] Inventors: Tyrone L. Hardy; Laura D. Brynildson, both of Albuquerque, N. Mex.

[73] Assignee: Medical Instrumentation and Diagnostics Corporation, San Diego, Calif.

[*] Notice: The portion of the term of this patent subsequent to Jan. 5, 2010 has been disclaimed.

[21] Appl. No.: 936,797

[22] Filed: Aug. 28, 1992

Related U.S. Application Data

[63] Continuation-in-part of Ser. No. 552,256, Jul. 11, 1990, Pat. No. 5,176,689, which is a continuation-in-part of Ser. No. 428,242, Oct. 27, 1989, abandoned, which is a continuation-in-part of Ser. No. 290,316, Dec. 23, 1988, Pat. No. 5,099,846.

[51] Int. Cl.$^5$ .............................................. A66B 19/00
[52] U.S. Cl. .................................... 606/130; 378/206
[58] Field of Search ................. 128/653.1; 606/130, 606/2, 11, 13; 378/20, 162–163, 165, 205–206; 607/88–93

[56] References Cited

U.S. PATENT DOCUMENTS

| | | | |
|---|---|---|---|
| 3,508,552 | 4/1970 | Hainault | 606/130 |
| 3,783,251 | 1/1974 | Pavkovich | 235/151 |
| 3,987,281 | 10/1976 | Hodes | 235/151.3 |
| 4,079,450 | 3/1978 | Grimm et al. | 364/200 |
| 4,123,143 | 10/1978 | Yachin et al. | 350/171 |
| 4,223,227 | 9/1980 | Horwitz | 250/491 |
| 4,230,117 | 10/1980 | Anichkov | 128/303 |
| 4,259,725 | 3/1981 | Andrews et al. | 364/521 |
| 4,278,888 | 7/1981 | Wagner | 205/445 |
| 4,341,220 | 7/1982 | Perry | 128/630 |
| 4,350,159 | 9/1982 | Gouda | 606/130 |
| 4,386,602 | 6/1983 | Sheldon et al. | 128/4 |
| 4,455,609 | 6/1984 | Inamura et al. | 364/414 |
| 4,463,758 | 8/1984 | Patil et al. | 128/303 |
| 4,502,147 | 2/1985 | Michaels | 378/206 |
| 4,583,538 | 4/1986 | Onik et al. | 128/303 |
| 4,597,380 | 7/1986 | Raif et al. | 128/6 |
| 4,598,368 | 7/1986 | Umemura | 364/414 |
| 4,608,635 | 8/1986 | Osterholm | 364/414 |
| 4,608,977 | 9/1986 | Brown | 128/303 |
| 4,617,925 | 10/1986 | Laitenen | 128/303 |
| 4,638,798 | 1/1987 | Shelden et al. | 606/130 |
| 4,651,732 | 3/1987 | Frederick | 128/303 |
| 4,702,571 | 10/1987 | Barber | 350/516 |
| 4,706,665 | 11/1987 | Gouda | 606/130 |

(List continued on next page.)

FOREIGN PATENT DOCUMENTS

| | | | |
|---|---|---|---|
| 2384481 | 11/1978 | France | 606/2 |
| 1074239 | 12/1988 | U.S.S.R. | 359/363 |

OTHER PUBLICATIONS

B. Bauer–Kirpes et al., "Computerized Optimization of $^{125}$I Implants in Brain Tumors," *J. Radiation Oncology Biol. Phys.*, vol. 14,4 No. 5, pp. 1013–1023 (May 1988).

Federico Colombo et al., "External Stereotatic Irradiation by Linear Accelerator," *Neurosurgery*, vol. 16, No. 2, pp. 154–159 (1985).

(List continued on next page.)

Primary Examiner—Angela D. Sykes
Attorney, Agent, or Firm—Dennis F. Armijo; Jeffrey D. Myers; Deborah A. Peacock

[57] ABSTRACT

A method and apparatus for determining, in three dimensions, the location, size, depth and width of tumors, lesions, abnormalities, structures, and the like, particularly useful for stereotactic surgery. The invention utilizes several energy beams which, when they intersect, allow for such measurements and calculations. In one embodiment, the energy sources attach to a stereotactic frame. In an alternative embodiment, the energy sources are incorporated within a stereotactic microscope. Either embodiment may be mounted on an articulated robotic type arm.

27 Claims, 20 Drawing Sheets

U.S. PATENT DOCUMENTS

| | | | |
|---|---|---|---|
| 4,729,098 | 3/1988 | Cline et al. | 364/414 |
| 4,729,099 | 3/1988 | Iverson et al. | 364/414 |
| 4,777,598 | 10/1988 | Kellar et al. | 364/413.22 |
| 4,790,026 | 12/1988 | Gennery et al. | 382/49 |
| 4,791,934 | 12/1988 | Brunnett | 128/653 |
| 4,813,588 | 3/1989 | Srivastava et al. | 228/103 |
| 4,832,049 | 5/1989 | Matsushita et al. | 128/781 |
| 4,856,528 | 8/1989 | Yang et al. | 128/653 |
| 4,884,566 | 12/1989 | Mountz et al. | 128/303 |
| 4,888,713 | 12/1989 | Falk | 364/522 |
| 4,905,702 | 3/1990 | Foss | 128/665 |
| 4,919,516 | 4/1990 | Petran et al. | 350/171 |
| 4,976,680 | 12/1990 | Hayman et al. | 600/7 |
| 4,977,505 | 12/1990 | Pelizzari | 364/413.19 |
| 5,027,818 | 7/1991 | Bova et al. | 128/653 |
| 5,099,846 | 3/1992 | Hardy et al. | 128/653.1 |
| 5,143,076 | 9/1992 | Hardy et al. | 128/664 |
| 5,176,689 | 1/1993 | Hardy et al. | 606/130 |

OTHER PUBLICATIONS

Antonio A. F. DeSalles, "Stereotaxic Applications." presented at UCLA Hands-On Sterotatic Surgery and Radiosurgery Workshop, Workbook pp. 11–26, University of California, Los Angeles, Aug. 20–22, 1992.

W. A. Friedman et al., "The University of Florida Radiosurgery System," Elsevier Science Publishing Company, Inc., *Surg. Neurol.*, vol. 32, pp 334–342 (1989).

Braton L. Guthrie et al., "Neurosurgical Operating Arm: Frameless Localization System for Planning and Performing Cranial Surgery," presented at UCLA Hands-On Stereotatic Surgery and Radiosurgery Workshop, Workbook pp. 39–51, University of California, Los Angeles, Aug. 22–22, 1992.

Tyrone L. Hardy, "Stereotatic CT Atlases," *Modern Stereotatic Surgery*, L. D. Lunsford, Ed., Boston, pp. 425–439 (1988).

Tyrone L. Hardy et al., "CASS: A Program For Computer Assisted Stereotaxic Surgery" *Proceedings of the 5th Annual Symposium on Computer Application in Medical Care*, Washington, D.C., pp. 1116–1126 (Nov. 1981).

Tyrone L. Hardy et al., "Computer-Assisted Stereotactic Surgery," *Appl. Neurophysiol.*, vol. 45, pp. 396–398 (1982).

Tyrone L. Hardy et al., "Computer Graphics with Computerized Tomography for Functional Neurosurgery," *Appl. Neurophysiol.*, Reprint, vol. 46, pp. 217–226 (1983).

Tyrone L. Hardy et al., "A Portable Computerized Tomographic Method for Tumor Biopsy," *Acta. Neurochir.* (Suppl.), p. 444 (1983).

P. J. Kelly et al., "Computer-Assisted Stereotatic Laser Microsurgery for the Treatement of Intracranial Neoplasms," *Neurosurgery*, vol. 10, No. 3, pp. 324–331 (1982).

P. J. Kelly et al., "Computer Simulation for the Stereotatic Placement of interstitial Radionuclide Sources onto CT-Defined Tumor Volumens," *Neurosurgery*, vol. 14, No. 4, pp. 442–448 (1984).

M. Koslow et al., "Stereotatic Surgical System Controlled by Computed Tomography," *Neurosurgery*, vol. 8, No. 1, pp. 72–82 (Jan. 1981).

D. Lefkopoulos et al., "The Ill-Conditioning in Stereotaxic Irradiation: Optimization of Isodoses Arrays Distribution Using the Singular Values Decomposition," *Eighth International Conference*, pp. 1129–1140 (Jun. 8–10, 1988).

W. Bruce Leggett et al., "Surgical Technology-The Viewing Wand, A New System for Three-Dimensional Computer Tomography-Correlated Intraoperative Localization," *Current Surgery*, pp. 674–677, presented at UCLA Hands-On Stereotatic Surgery and Radiosurgery Workshop, Workbook pp. 399–403, University of California, Los Angeles, Aug. 20–22, 1992 (Dec. 1991).

A. R. Parkinson et al., "Exploring Design Space: Optimization as Synthesizer of Design and analysis," *Computers in Mechanical Engineering*, pp. 28–36 (Mar. 1985).

T. M. Peters et al., "The Role of Computed Tomography and Digital Radiographics Techniques in Stereotatic Procedures for Electrode Implanation and Mapping, and Lesion Localization," *Appl. Neurophysiol.* vol. 46, pp. 200–205 (1983).

R. K. Rice et al., "Measurements of Dose Distributions in Small Beams of 6MV X-Rays," *Phys. Med. Biol.*, vol. 32, No. 9, pp. 1087–1099 (1987).

C. H. Shelden et al., "Development of Computerized Microstereotaxis Method for Localization and Removal of Minute CNS Lesions Under Direct 3-D Vision," *Journal of Neurosurgery*, Technical Report, vol. 52, pp. 21–27 (Jan. 1980).

C. J. Thompson et al., "A System for Anatomical and Functional Mapping of the Human Thalamus" *Comput. Biomed. Res.*, Textbook, vol. 19, pp. 9–24 (1977).

K. Weaver et al., "A CT-Based Computerized Treatment Planning System for I-125 Stereotatic Brain Im- (List continued on next page.)

OTHER PUBLICATIONS plants," *J. Radiation Oncology Biol. Phys.*, vol. 18, No. 2, pp. 445–454 (1989).

K. R. Winston et al., "Linear Accelerator as a Neurosurgical Tool for Stereotatic Radiosurgery," *Neurosurgery*, vol. 22, No. 3, pp. 454–462 (1988).

Advertisement, "The Idea That Stereotaxy Could Bring More Precision to Microsurgery is no Longer a Possibility," Leksell Micro-Stereotatic System, distributed by Electa Instruments AB, Stockholm Sweden, Elekta Instruments, Inc., Decatur, Ga.

Brochure, "Microscope Support System-Surgical Robot," DeeMed, A GT Technologies Group Companies, Domene, France and Atlanta, Ga.

Brochure, "The Viewing Wand-Technical Specifications," ISG Technologies, Inc., Ontario, Canada.

Brochure, "Hardware and Software for Computer Assisted CT and MRI Based Stereotactic Neurosurgery," Stereotatic Medical Systems, Inc. (no date).

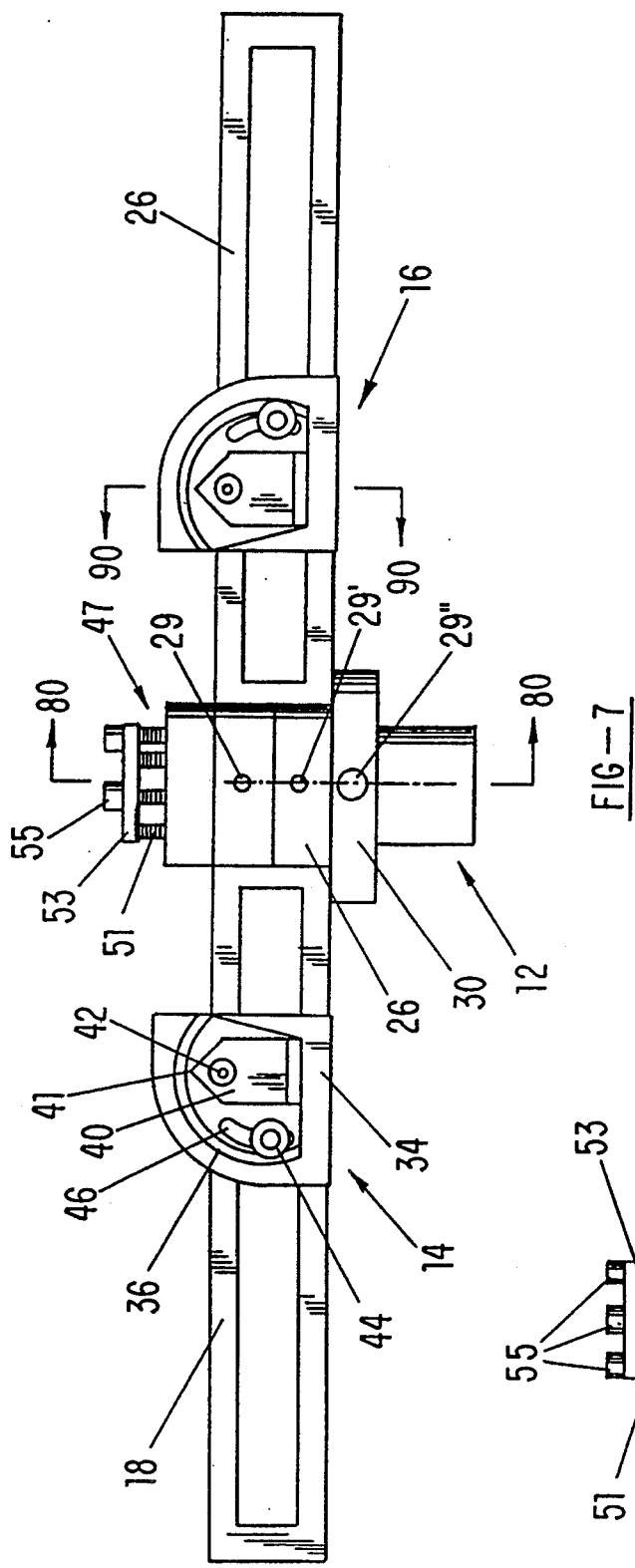

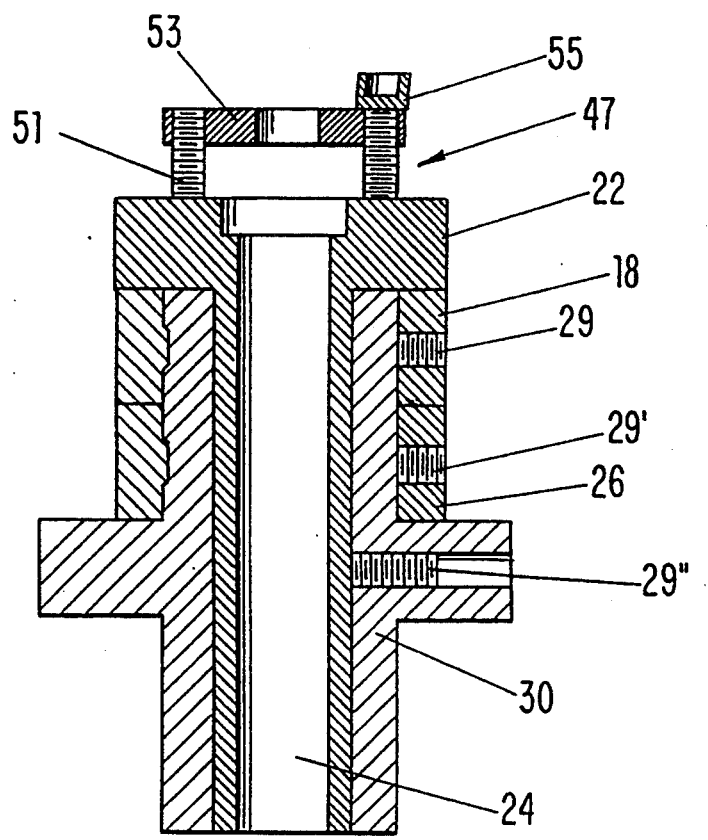
FIG—9
SECTION 80-80
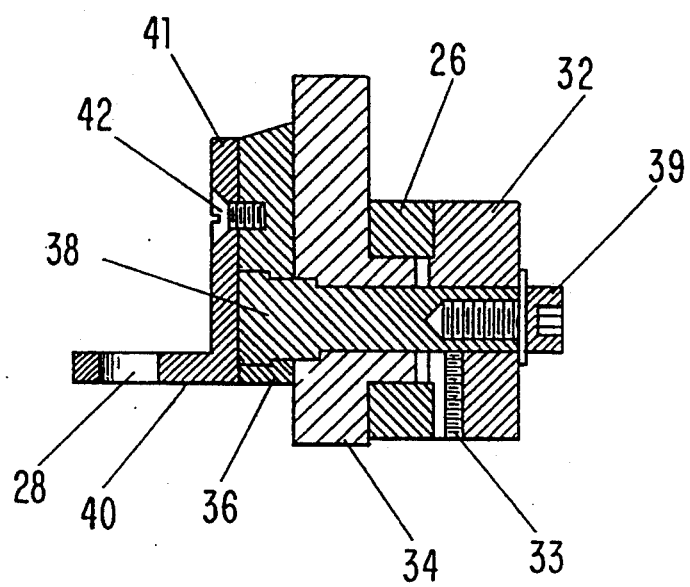
FIG—10
SECTION 90-90

SECTION 80-80

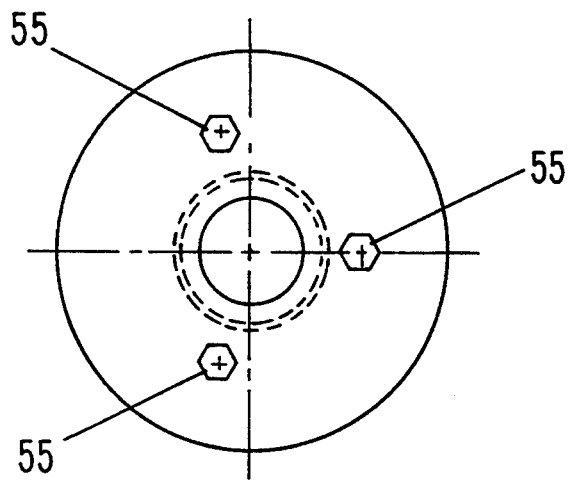
FIG—17
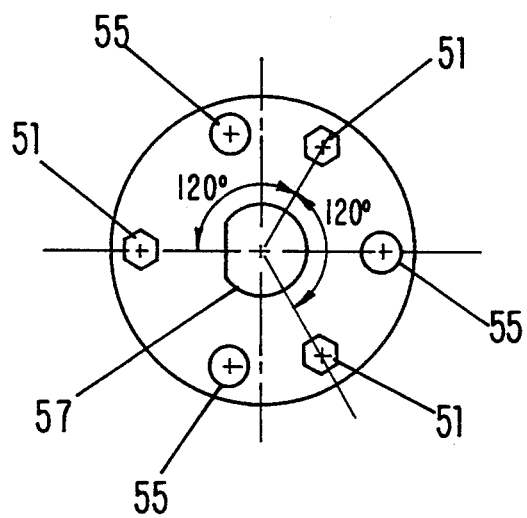
FIG—18
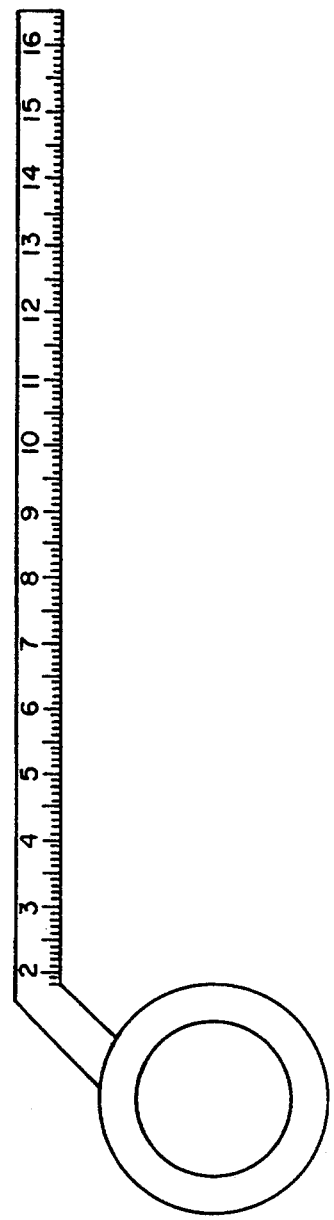
FIG—19

FIG—36

THREE-DIMENSIONAL BEAM LOCALIZATION APPARATUS AND MICROSCOPE FOR STEREOTACTIC DIAGNOSES OR SURGERY MOUNTED ON ROBOTIC TYPE ARM

CROSS-REFERENCE TO RELATED PATENT APPLICATION

This application is a continuation-in-part application of U.S. patent application Ser. No. 07/552,256, entitled *Three-Dimensional Beam Localization Apparatus for Stereotactic Diagnoses or Surgery*, to Hardy et al., filed Jul. 11, 1990, now U.S. Pat. No. 5,176,689, which is a continuation-in-part application of U.S. patent application Ser. No. 07/428,242, entitled *Three-Dimensional Laser Localization Apparatus and Method for Stereotactic Diagnoses or Surgery*, to Hardy et al., filed Oct. 27, 1989, now abandoned, which is a continuation-in-part application of U.S. Pat. No. 5,099,846, U.S. patent application Ser. No. 07/290,316, entitled *Method and Apparatus for Video Presentation From a Variety of Scanner Imaging Sources*, to Hardy, filed on Dec. 23, 1988, and issued on Mar. 31, 1992, as U.S. Pat. No. 5,099,846. Related application are U.S. Pat. No. 5,143,076, U.S. patent application Ser. No. 07/552,164, entitled *Three-Dimensional Beam Localization Microscope Apparatus for Stereotactic Diagnoses or Surgery*, to Hardy et al., filed on Jul. 11, 1990, and issued Sep. 1, 1992, as U.S. Pat. No. 5,143,076, which was a divisional application of the '242 patent application; U.S. patent application Ser. No. 07/860,926, now allowed, entitled *Method and Apparatus for Video Presentation from a Variety of Scanner Imaging Sources*, to Hardy, filed Mar. 31, 1992; U.S. patent application Ser. No. 07/534,974, entitled *Three-Dimensional Computer Graphics Simulation and Computerized Numerical Optimization for Dose Delivery and Treatment Planning*, to Hardy et al., filed Jun. 8, 1990, and issued Apr. 27, 1993, as U.S. Pat. No. 5,205,289; U.S. patent application Ser. No. 07/500,788, now abandoned, entitled *Three-Dimensional Graphics Simulation and Actual Imaging Data Composite Display*, to Hardy, filed Mar. 28, 1990; and U.S. patent application Ser. Nos. 07/916,018, now abandoned and 07/712,252, now abandoned entitled *Method and Apparatus for Achieving and Displaying Anatomico-Physiological Data in a Normalized Whole Brain Mapping and Imaging System*, to Hardy et al., filed Jul. 17, 1992, and Jun. 6, 1991, respectively. The teachings of all of the above patents and patent applications are incorporated herein by reference.

BACKGROUND OF THE INVENTION

1. Field of the Invention

The present invention relates to a method and apparatus for providing three-dimensional beam localization for stereotactic diagnoses or surgery. The invention comprises a fixed centrally disposed beam source and at least one additional movable beam source which allows for measurement and calculations of depth, width and position of lesions, tumors, abnormalities, structures, and the like.

2. Description of the Related Art Including Information Disclosed Under 37 C.F.R. §§197-199

The general types of operative neurosurgical procedures are open operative techniques, stereotactic operative techniques, and a combination of open operative with stereotactic techniques. These are discussed below.

Open Operative Techniques

Open operative approaches to the brain have been present since antiquity. Typical presently practiced techniques generally involve reflecting the scalp and subcutaneous tissue off of the underlying skull after which a variable size opening to expose the inner cranial contents is subsequently made. The cranial opening is generally tailored to allow adequate instrument access to an intercranial structure and/or lesion. Such techniques require direct visualization of the structure in question. For example, such approaches are commonly used for the localization, identification, and removal of a tumor within the brain itself. A significant difficulty of this approach involves the exact localization and tailoring of the cranial opening for surgical approach and resection of, for example, a tumor. In addition, the exact localization of a lesion in the depths of the brain is frequently not readily apparent from inspection of the overlying brain.

Techniques utilizing various kinds of measurements based on anthropomorphic proportioning in relation to various kinds of diagnostic imaging have been used to approximate the location of intracerebral structures and/or lesions. The location of "large" structures and/or lesions can usually be fairly easily determined with these techniques. This is not true, however, for a "small" deep-seated intracerebral lesion where no telltale evidence of its position is apparent from viewing the overlying cerebral mantel. Other techniques, such as stereotactic surgery, have been used to more precisely indicate the spatial localization of such areas as defined within the confines of a stereotactic surgical frame system.

Stereotactic Operative Techniques

The aim of the stereotactic operative technique is to allow physiological exploration and/or destruction of deep cerebral or spinal cord structures which are invisible from the surface, but which location can be determined by a knowledge of their coordinates in space relative to known anatomical and topographical landmarks. The use of stereotaxis in neurosurgical techniques generally seeks to avoid open operative approaches to these areas and cause minimum disturbance to surrounding structures. The technique generally involves the placement of fine electrodes or probes in strategic "target areas," which may be a specific functional anatomical site, a morphological lesion, or an abnormality. Some additional examples are stereotactic radio surgery wherein the principles of stereotaxy are used to project a series of radiation beams into an intracerebral area or lesion, One of the major difficulties in stereotactic surgery is graphic conceptualization of the location of surgical probes inserted into deep brain structures. Not only is the probe out of the surgeon's sight, but it is tilted, rotated, and extended in many different directions, which makes it almost impossible for the surgeon to maintain a mental picture of where the probe is in the brain core. He must imagine the location of the probe while taking into account the forward and lateral angles of the probe, the distance of the probe from the target, the direction that the electrode extends from the probe, and many other angular variables. Furthermore, the coordinate system of the stereotactic frame seldom corresponds to the "brain coordinate system," thereby causing more room for error and more difficulty in placement of the probe. Traditional stereotactic surgery, therefore, is essentially a "blind" surgical procedure with many complex geometric variables.

Combined Open Operative and Stereotactic Operative Techniques

Some of the difficulties inherent in the open operative and the stereotactic operative techniques can be somewhat ameliorated by combining the two techniques in an operative procedure. This has classically been done by the spatial localization of an intracranial structure and/or lesion by the stereotactic localization technique, in which the patient's head is fixed in a stereotactic surgical frame, and the use of a surgical cranial opening tailored to allow adequate direct visualization and access to an intercranial structure and/or lesion. This combined technique, therefore, allows direct visualization of an intracranial structure and/or lesion for surgery. The disadvantage of this technique, as developed to date, has been the three-dimensional volumetric determination of an intracerebral structure and/or lesion in stereotactic space and its shifting position due to gravitational and positional changes of the brain occasioned by its exposure to the atmosphere and the surgical retraction of overlying brain tissue during the course of the subsequent exposure of the underlying brain structure and/or lesion.

Several methods of combined open operative and stereotactic techniques have been developed for the localization and resection of intracerebral structures and/or lesions. The following publications set forth examples of such general principles of localization:

1. Kelly, P. J., Alker, George J., Jr., and Georse, Stephan, "Computer-Assisted Stereotactic Laser Microsurgery for the Treatment of Intracranial Neoplasms", Neurosurgery, Vol. 10, pp. 324–331 (1982).

2. Koslow, M. Abele, M. G., Griffith, R. C., Mair, G. A., and Chase, N. E., "Stereotactic Surgical System Controlled by Computed Tomography," Neurosurgery, Vol. 8, pp. 72–82 (1981).

3. Shelden, C. H., McCann, G., Jacques, S., Luter, H. R., Frazier, R. E., Katz, R., Kuki, R., "Development of a Computerized Microstereotaxis Method for Localization and Removal of Minute CNS Lesions Under Direct 3-D Vision," *Journal of Neurosurgery*, Technical report, Vol. 52, pp. 21–27 (1980).

4. A stereotactic helium neon laser light pointer distributed by A. B. Elekta Instruments.

The techniques involved in these publications herein noted consist of the following:

1. A stereotactic frame system fixable about a patient's head is used in conjunction with various imaging technologies, e.g., plain X-ray, computerized tomographic scans, magnetic resonance imaging scans, and stereotactic angiography, to locate deep seated intracerebral lesions and stereotactic space.

2. Various stereotactic volumetric determinations with transformation algorithms have been used to simulate the position of the tumor in the stereotactic space. These, however, do not take into consideration positional and gravitational shifts of a lesion as noted above.

3. Many current techniques incorporate a laser light pointer along the course (tract) in which a surgeon might encounter a lesion or tumor. The position of the tumor, however, frequently varies from its original position as determined from various types of diagnostic imaging, due to patient position, e.g. sitting up or lying down, pressure changes, and the like. No good marker prior art techniques have been developed to accurately define the tumor margins (which are subsequently used to determine tumor volume) or to compensate for positional shifts of a tumor or lesion.

Several patents disclose methods and devices which are attempts to better localize a tumor, or the like, using a stereotactic frame. None, however, provide the three-dimensional accuracy of the present invention, nor utilize the localization method and apparatus of the present invention. These patents are discussed below.

U.S. Pat. No. 3,508,552, entitled *Apparatus for Stereotaxic Neurosurgery*, to Hainault, et al., discloses the use of multiple grids for use in conjunction with an x-ray device to determine a passage for the surgeon to enter the brain. U.S. Pat. No. 4,350,159, entitled *Frame for Stereotactic Surgery*, to Gouda, teaches the use of radio-opaque vertical markers on a stereotactic frame for alignment purposes.

U.S. Pat. No. 4,638,798, entitled *Stereotactic Method and Apparatus for Locating and Treating or Removing Lesions*, to Shelden, et al., and U.S. Pat. No. 4,706,665, entitled *Frame for Stereotactic Surgery*, to Gouda, both disclose a procedure and apparatus for locating and removing a brain tumor using a series of CT scans to locate the tumor and an adjustable stereotactic frame to support probes and instruments in a three-dimensional arrangement, indicated by the scans.

French Patent 2384481, entitled Stereotaxic Apparatus, to Hubert, et al., discloses the use of a laser and mirrors to align the X-ray beam, useful in medical stereotaxy.

None of the above-described methods or devices are able to translate to the surgeon the three-dimensional boundaries of the lesion as resection takes place.

U.S. Pat. No. 5,099,846, entitled *Method and Apparatus for Video Presentation From a Variety of Scanner Imaging Sources*, filed on Dec. 23, 1988, to Hardy, relates to a three-dimensional stereotactic technique, utilizing various scanner imaging sources, to assist a surgeon or health practitioner in locating and measuring lesions, tumors, abnormalities, structures, and the like. The '316 application is useful in conjunction with the present invention.

U.S. patent application Ser. No. 07/428,242, entitled *Three-Dimensional Laser Localization Apparatus and Method for Stereotactic Diagnoses or Surgery*, filed on Oct. 27, 1989, to Hardy, et al., now abandoned, provides for three-dimensional laser localization for stereotactic diagnoses or surgery. In the preferred embodiment of that invention, there were difficulties in calibration (e.g., the trajectory of the laser beams). The present invention overcomes these problems and provides for easy and accurate calibration of the various parameters.

SUMMARY OF THE INVENTION

The present invention relates to a stereotactic surgical beam localization apparatus attachable to a stereotactic frame. The apparatus comprises means for emitting at least two (and preferably three or more) beams from separate and spaced points; means for attaching the beam emitting means on a frame; means for movably adjusting the relative positions with respect to one another of the beam emitting points; means for aiming the beams at user selected locations on a body; and means for ascertaining desired information about a selected volumetric entity of the body from the positions of the beam emitting means in the apparatus, the relative positions with respect to one another of the beam emitting means, and the aiming directions of beams from the first and second beam emitting points. The mounting frame is attached to the stereotactic frame. The beam emitting means may be positioned on the mounting frame along an arc or tangent of the stereotactic frame, in a linear, spherical, or planar relationship.

Desired information about the selected volumetric entity of the body is determined by proportional angulation methods using information about the positions of the beam emitting sources on the frame, the positions of the beam emitting sources relative to one another, and the aiming directions of the beams from the beam emitting sources. Information about a point, area or volume of the volumetric entity can be determined by using a series of selected data points.

In the preferred embodiment, there are at least three beam emitting sources, with one of such beam emitting sources being a fixed, centrally disposed beam emitting source, with the additional beam emitting sources being movably adjustable, spaced from and independent of one another and the fixed centrally disposed beam source. The fixed centrally disposed beam is aimed at a predetermined, fixed location of the selected volumetric entity of the body. The additional beams are variably aimed at additional selected locations of the selected volumetric entity of the body. The additional beam emitting sources are movably adjustable by micrometer positioning or by digital means.

In the preferred embodiment, the apparatus comprises a separate wing member for each of the additional beam emitting sources, with the beam emitting source longitudinally movable on the wing member and pivotally movable such that the beams emitted therefrom can move between a 0° to 90° arc relative to the fixed centrally disposed beam. One or more of the wing members are rotatable, up to 360°, about the fixed centrally disposed beam emitting means.

The preferred beam emitting source comprises a light beam source, such as a laser, with fiber optics connections. Alternatively, the beam emitting source comprises laser diodes, x-ray beams, heavy particle beams, anti-matter beams, proton beams, gamma beams, ultrasonic beams, infrared beams, nuclear rays, other beams and rays, and the like.

The invention further comprises a method of determining desired information about a volumetric entity in a body. This method comprises the following steps:

a) positioning a plurality of beam sources on an apparatus fittable on the body;

b) adjusting the spacing and the rotational positions of the beam sources relative to one another so that the beams emitted therefrom intersect at a point on the volumetric entity of the body; and c) using proportional angulation, determining positional information about the entity.

Steps b) and c) may be repeated a multiplicity of times to a series of points on an area or volume of the volumetric entity to determine positional, area, and volumetric information about the volumetric entity.

In an alternative embodiment, the invention can be housed with an adapter which can be attached to an articulating robotic type arm, the base of which can be attached to a stereotactic frame or other component of a stereotactic localization system. The robotic type arm can serve to stereotactically position the beam localization apparatus such that the spatial positions of the articulating arm and the beam localization apparatus can mathematically define points or volumes within a given stereotactic space.

Accordingly, it is a primary object of the present invention to localize and determine the fixed, varying or changing position of selected lesions, tumors, abnormalities, structures, and the like, in a body.

It is another object of the present invention to measure and calculate the widths, depths, and positions of selected lesions, tumors, abnormalities, structures, and the like, in a body.

Yet another object of the present invention is to provide an apparatus for stereotactic surgery, which can be attached to a stereotactic frame.

Additional objects, advantages and novel features of the invention will be set forth in part in the description which follows, and in part will become apparent to those skilled in the art upon examination of the following or may be learned by practice of the invention. The objects and advantages of the invention may be realized and attached by means of the instrumentalities and combinations particularly pointed out in the appended claims.

BRIEF DESCRIPTION OF THE DRAWINGS

The accompanying drawings, which are incorporated into and form a part of the specification, illustrate several embodiments of the present invention and, together with the description, serve to explain the principles of the invention. In the drawings:

FIG. 7 is a front view of the preferred frame system of the present invention;

FIG. 8 is an end view of the frame system of FIG. 7;

FIG. 9 is a cross-sectional view along section 80—80 of FIG. 7;

FIG. 10 is a cross-sectional view along section 90—90 of FIG. 7;

FIG. 17 is a top view of the shaft of FIG. 7;

FIG. 18 is a top view of the adjusting or mounting stage of FIG. 7;

FIG. 19 is a top view of one of the side horizontal wings of FIG. 7, showing markings;

DETAILED DESCRIPTION OF THE PREFERRED EMBODIMENTS OF THE INVENTION

Figure 1:
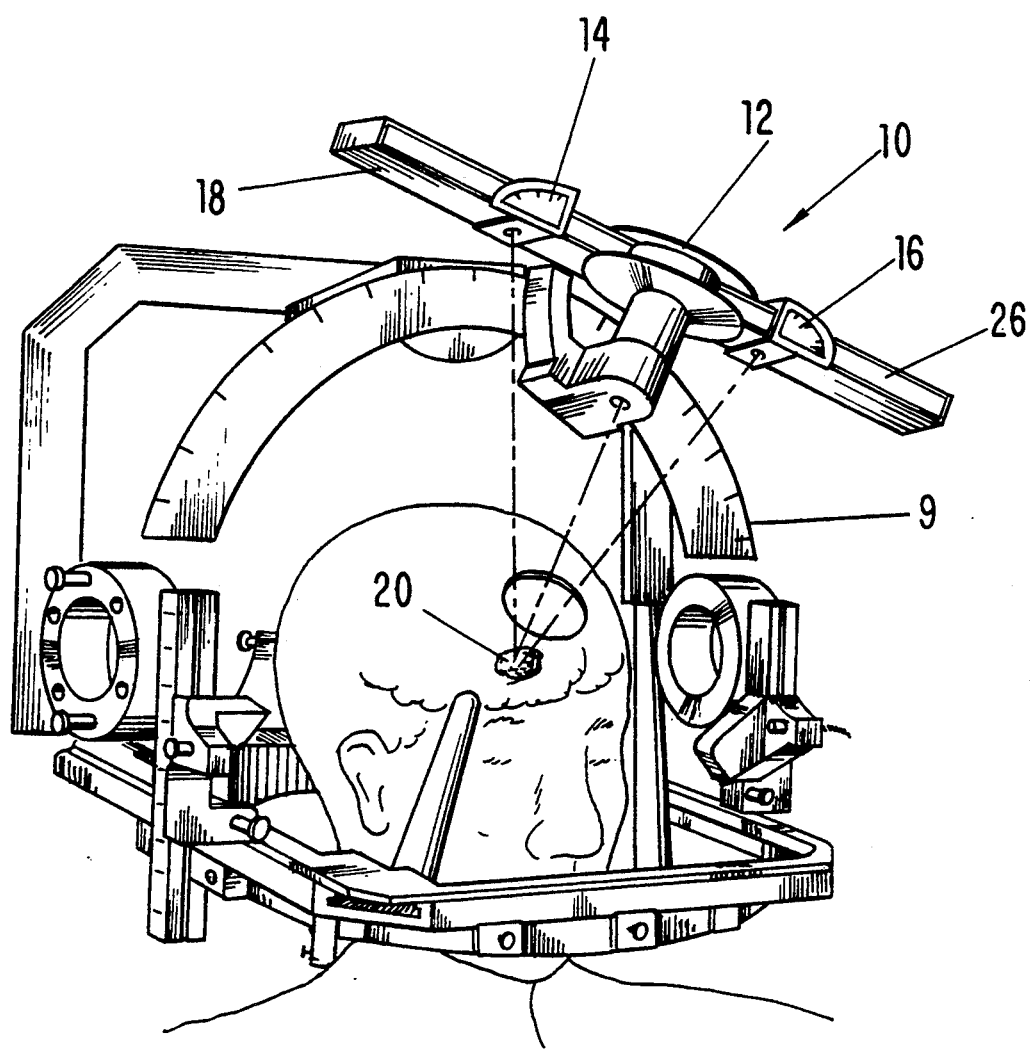
FIG. 1 is a perspective view of the preferred laser localization apparatus of the present invention showing a fixed centrally disposed light source, and two additional light sources.

The beam localization apparatus and method of the present invention utilize several spaced beam sources for three-dimensional localization and measurement of lesions, tumors, abnormalities, structures, and the like (generally referred to herein as "lesions" or "tumors"), in a selected part of a human or animal body, particularly in a brain, (generally referred to in the specification and claims as "entity", "volumetric entity" or "area to be measured" or "volume to be measured" or "brain"). The invention is particularly useful in conjunction with a medical stereotactic frame. Although the term "stereotactic frame" is customarily used in the art to denote a stereotactic frame attachable to a head, this term, for the purposes of the present invention, means a frame which is attachable to any part of the body. The invention is not limited to surgical or diagnostic methods for the head or brain, but can also be used on other parts of the body, e.g. the spine, with a frame system suitable for such body parts (e.g. a cylindrical coordinate system for a spinal stereotactic frame).

The term "beam" as used throughout the specification and claims is intended to include all useful beams and rays, such as laser beams, x-ray beams, heavy particle beams, anti-matter beams, proton beams, gamma beams, ultrasonic beams, infrared beams, nuclear rays, other beams and rays, and the like. The preferred embodiment shown in the drawing utilizes laser beams, but the invention is not limited to the use of light beams.

The invention involves a central light beam from a beam emitting source, such as a laser, which is projected along a previously determined stereotactic radian along the course of which the selected volumetric entity of the body may be located. Adjacent to this central beam source are several (preferably at least two) additional side beam emitting sources which emit "side beams", such as laser beams, which are projected from known positions relative to the central beam source. Such positioning depends upon the structure of the stereotactic frame system. For example, in a spherical coordinate system the additional beam emitting sources can be located along either a tangent to the arc or an arc of a stereotactic frame. The side beam sources are moveable along such arcs or tangents so that they can be positioned accurately in relationship to the central beam source. The central beam and the side beam can originate from a single source and by using optical equipment, such as mirrors, prisms, and lasers, can be made to project from three spaced points. The beams can alternatively originate from two, three or more sources and rely on mirrors, prisms, or lasers. Laser diodes can be used to provide the beams. The angles of the side beams are variable in a number of fashions so that they can be made to intersect the central beam at varying points along the central beam's trajectory. This capability allows calculations of depths along the trajectory of the central beam for determining the near and far positions of the volume of the selected volumetric entity of the body, such as an intracerebral structure and/or lesion, in three-dimensional space such calculations are performed by proportional angulations. Also derived from the ability to vary the angles of the additional or side beams is the capacity to determine the projected boundaries of the volume of the lesion in three-dimensional space in a full spherical manner. Measurements of a three-dimensional volume can be determined from various angles of beam intersection as discussed below.

FIGS. 1–30 illustrate a preferred embodiment of a localization laser apparatus of the present invention comprising a beam localization frame system 10 having a centrally disposed, fixed light source 12 and two moveable side light sources 14 and 16 disposed on side horizontal wings or tracks 18 and 26, which are attachable to a stereotactic frame 9 (see FIG. 1). The stereotactic frame 9 may be one which is commonly available in the art. Centrally disposed light source 12 is preferably mounted in a fixed, centrally disposed position. Side light sources 14 and 16 each have horizontal motion along the horizontal tracks 18 and 26 independent of centrally disposed light source 12 and each other. Also as demonstrated in the drawings, light sources 14 and 16 are each independently, pivotally moveable in order to enable the surgeon or health practitioner to change the angle of each of their respective laser localization beams from a vertical aim through a 90° arc crossing the fixed vertical beam from light source 12. The light beams emitted from light sources 12, 14, and 16 are shown by dashed lines in the drawings.

Figure 2:
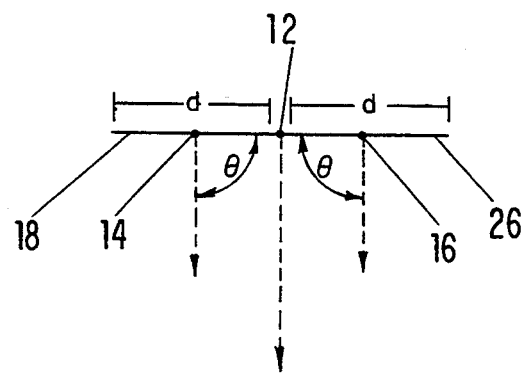
FIG. 2 is a diagram of the invention showing horizontal laser tracks with a fixed centrally disposed light source and two additional light sources.

FIGS. 2-6 illustrate, simply, how side light sources 14 and 16 (shown as points and also sometimes referred to as "points" in the specification and claims) move pivotally relative to centrally disposed, fixed light source 12 (also shown as a point) in the localization of a hypothetical tumor 20 (shown by a round circle). FIG. 2 illustrates all light beams from the light points or sources 12, 14, and 16 having a vertical aim. As can be readily seen, the side light sources 14 and 16 can pivot through a 90° arc (shown by the angle Θ markings on (FIG. 2). FIG. 2 also illustrates a range of possible horizontal movement (denoted as "d") for the side light sources 14 and 16, relative to the centrally disposed light source 12, along the side horizontal tracks 18 and 26 (shown by lines).

Figure 3:
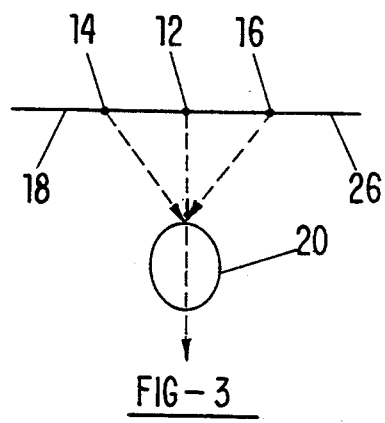
FIG. 3 is a diagram of the invention of FIG. 2 showing the localization of the top of a tumor.
Figure 4:
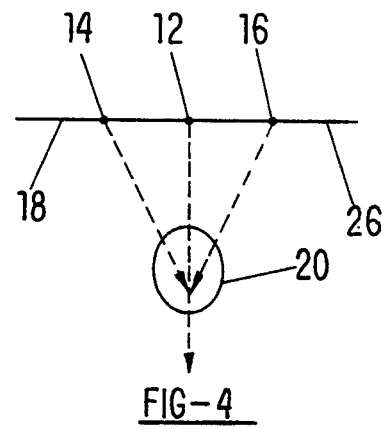
FIG. 4 is a diagram of the invention of FIG. 2 showing the localization of the bottom of the tumor.
Figure 5:
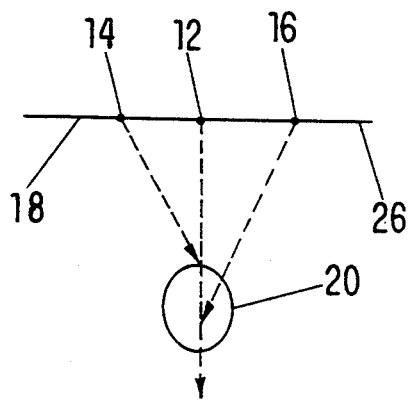
FIG. 5 is a diagram of the invention of FIG. 2 showing an alternative localization of the top and bottom of a tumor.
Figure 6:
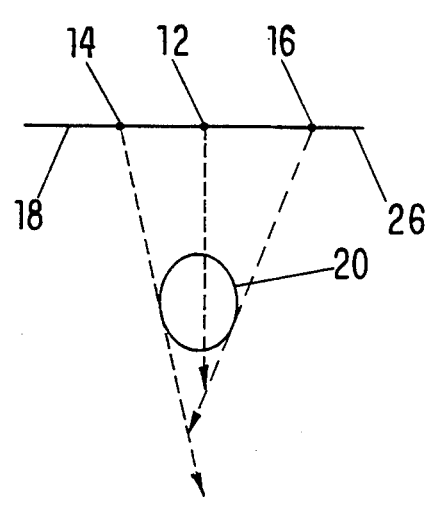
FIG. 6 is a diagram of the invention of FIG. 2 showing the localization of the sides or the width of the tumor.

FIGS. 3-6 illustrate the intersection of the beams for the localization of the tumor 20. In this example, centrally disposed beam source 12 has its beam aimed at the center of the tumor 20. Side beam sources 14 and 16 emit beams which intersect with the central beam from central beam source 12 to define the top, bottom, sides and general positioning of the tumor 20. FIG. 3 illustrates beams from side beam sources 14 and 16 intersecting the beam from centrally disposed source 12 to define the top of the tumor 20. FIG. 4 illustrates beams from side beam sources 14 and 16 intersecting the beam from centrally disposed beam source 12 to define the bottom of the tumor 20. FIG. 5 illustrates an alternative method of defining the top and bottom of the tumor 20 with the intersection of the side beams with the central beam. FIG. 6 illustrates beams from side beam sources 14 and 16 intersecting with the central beam from beam source 12 to define the edges or sides of the tumor 20. Side beam sources 14 and 16 are rotatable on a tangential plane all or a portion of 360° around central beam source 12. Hence, tumors or lesions of varying widths can be measured and located. Although these diagrams illustrate generally a two-dimensional working of the invention, those skilled in the art can appreciate that the side beam sources 14 and 16 are independently rotatable all or a portion of 360° on a tangential plane around the central beam source 12 and that more than two additional or side beam sources may be utilized in practicing the invention (e.g., see FIG. 32) to provide more precise localization and measurements. Likewise, a centrally fixed beam source and one additional beam source or two variable beam sources (with no centrally fixed beam source) may be used to practice the invention, using proportional angulation methods to make determinations, although such determinations will not be as precise as those obtained by utilizing three or more beam sources.

All measurements are easily determined using well known proportional angulation techniques, by knowing the distance of the point of intersection of each of the beams, the angles of the beams, and the rotations of the beam sources. Such calculations can be performed manually, or preferably with interactive software, and can be incorporated into or used in conjunction with other stereotactic methods and apparatuses, such as those disclosed in co-pending patent application, Ser. No. 07/290,316.

The present invention, using angulational determinations of three-dimensional spatial volumetrics and position can aid the surgeon or health practitioner to: (1) directly indicate the position of e.g. an underlying intracranial/intracerebral structure, such as a lesion or tumor within the confines of the skull, so that the size and position of an opening, such as a cranial opening, can be accurately tailored; (2) accurately determine the location of the lesion or tumor; (3) accurately determine for simulation with computer graphics simulation methodology, gravitational and positional shifts of the lesion or tumor; and (4) accurately measure the depth, width, and volume of the tumor or lesion. Desired information about the tumor is determined by proportional angulation methods using information about the positions of the beam sources, the positions of the beam sources relative to one another, and the directions of the beams from the beam sources. Information about a point, area or volume of the tumor can thereby be determined using a series of selected data points.

A preferred three-dimensional laser localization apparatus is shown in the perspective view of FIG. 1, and in greater detail in the plan views of FIGS. 7-30. As shown therein, the beam localization frame system 10 of the invention is attachable as a separate apparatus onto a stereotactic probe holder device or on a typical stereotactic frame 9. The present invention comprises a central light emitting source 12, such as a laser light source, and two or more additional or side light emitting sources 14 and 16 which are independently movable away from and towards the central light emitting source 12, along a tangent bar or arc of the frame system 10, such as on a horizontal wing or track 18 and 26. The side light sources 14 and 16 can be moved along a tangent or an arc carrier anywhere within a tangential plane or arc relative to the central light source 12. The side light sources 14 and 16 are also preferably adjustably variable in an angular or pivotally rotatable fashion by micrometer or digital positioning so that their relationships of beam intersection with the beam from the central light source 12 can be varied or changed within highly accurate parameters.

FIGS. 7 and 8 illustrate front and side views, respectively, of the preferred beam localization frame system 10 of the invention. FIGS. 9 and 10 illustrate cross-sectional views of sections 80—80, and 90—90, respectively, of FIG. 7. The two ends or sides of the beam localization frame system 10 are substantially similar and thus the discussion below which is applicable to one end only is also applicable, in general, to the other end. The beam localization frame system 10 comprises a centrally disposed shaft system 22 and a centrally disposed laser light mount 47 for mounting the central, fixed light source 12 and allowing the centrally disposed fixed light beam emitted therefrom to be emitted via central light emitting channel 24 (see FIGS. 8 and 9); and side horizontal wings 18 and 26 for mounting the side light sources 14 and 16 and allowing the light beams emitted therefrom to be emitted via separate light emitting channels 28 (see FIG. 10). As shown in FIG. 8, the vertical aim of all light beams is preferably aligned. FIG. 9 shows the central shaft 22 affixed to the beam localization frame system 10 by various set screws 29, 29' and 29". Set screw 29" is preferably recessed to avoid protrusion and obstruction of use of the frame 10. The side horizontal wings 18 and 26 are independently rotatably and movably mounted above a spindle 30.

FIG. 10 shows the relationship among a locking plate 32 with set screw 33, the side horizontal wing 26, a horizontal bezel carriage 34, a vertical azimuth bezel 36, a pivot pin 38, a pivot locking screw and washer 39, a focusing lens assembly bracket 40 which carries the side light emitting channel 28, and a holding screw 42. A bezel locking screw 44 assists in holding the vertical azimuth bezel 36 to the focusing lens assembly bracket (see FIGS. 7 and 8).

The focusing lens assembly bracket 40 which is fixed relative to the vertical azimuth bezel 36, can pivot, as adjusted by the surgeon, relative to the horizontal bezel carriage 34 which is affixed to the side horizontal mounting wing 18 or 26 and the locking plate 32. A sloped pointer 41 shows the surgeon the angle of the beam being emitted from the light emitting source 16 via the side light emitting channel 28. Bezel locking screw 44, which slides in sectional circular slot 46 disposed in the vertical azimuth bezel 36, holds the vertical azimuth bezel 36 and horizontal bezel carriage 34 in place along the horizontal wing 18 or 26 after the desired position is obtained, by compressing the vertical azimuth bezel 36 against the horizontal bezel carriage 34. Squeezing or compressing the vertical azimuth bezel 36 against the horizontal bezel carriage 34 provides for greater calibration of the invention and prevents the components from rocking. A number of screw positions (e.g., see FIG. 28 which has three screw positions 43) may be provided to allow a wide range of movement of the vertical azimuth bezel 36. Any number of screw positions could be provided in accordance with the invention.

Figure 11:
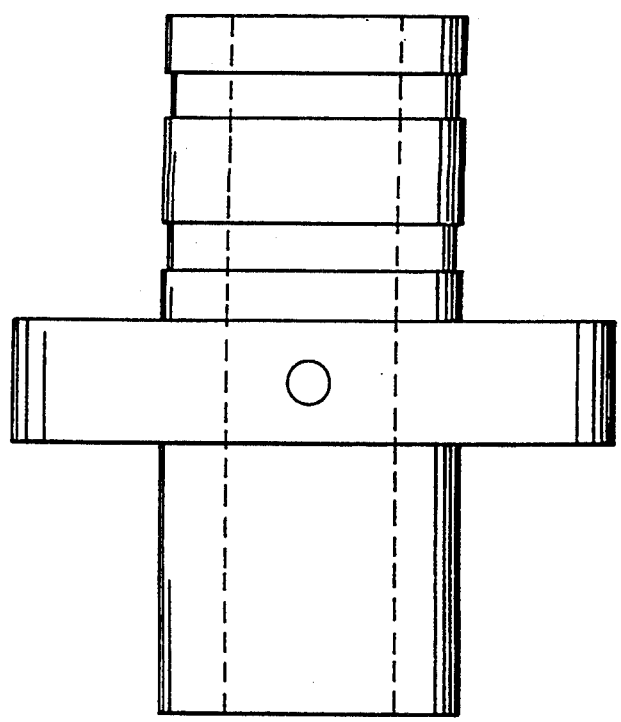
FIG. 11 is a side plan view of the spindle of FIG. 7.
Figure 12:
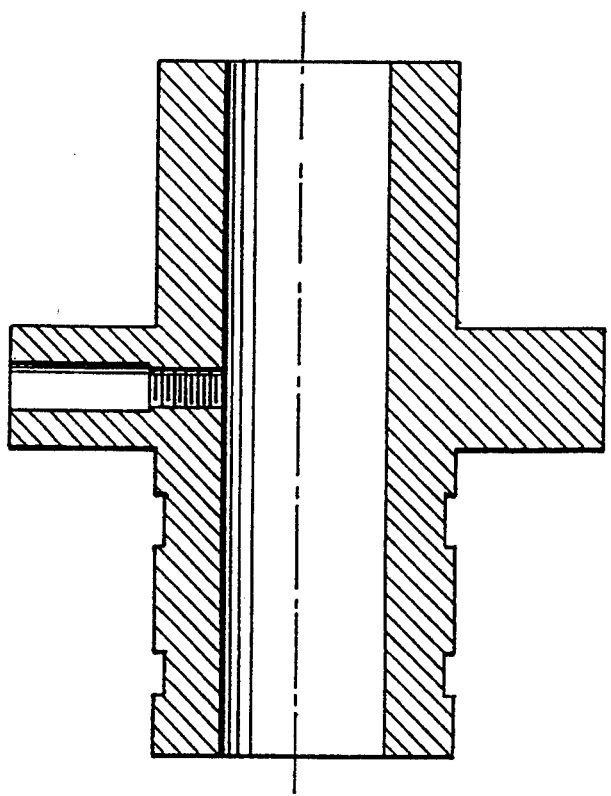
FIG. 12 is a cross-sectional side view of the spindle of FIG. 7.
Figure 13:
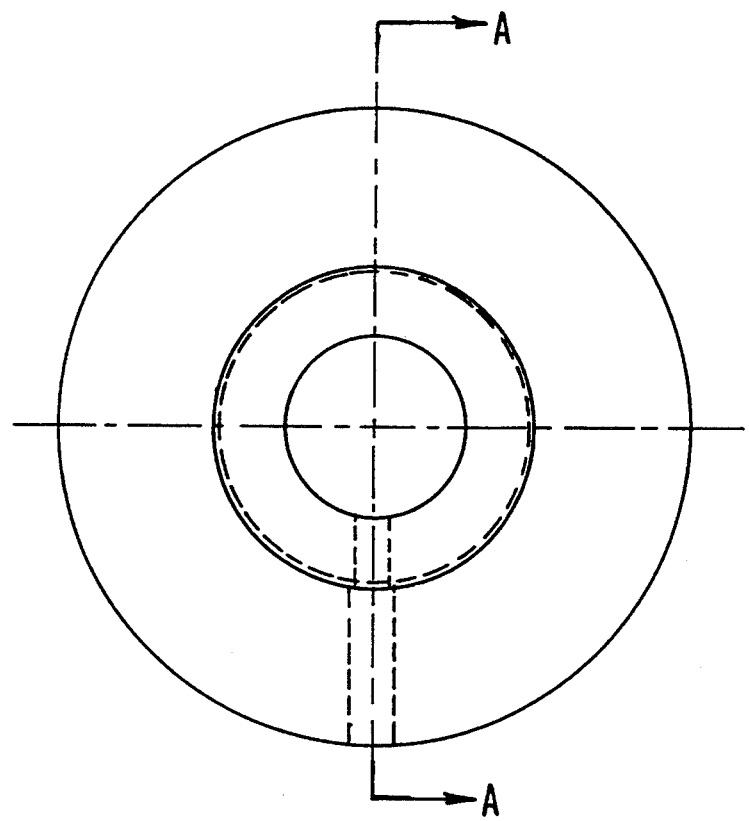
FIG. 13 is a top view of the spindle of FIG. 7.
Figure 14:
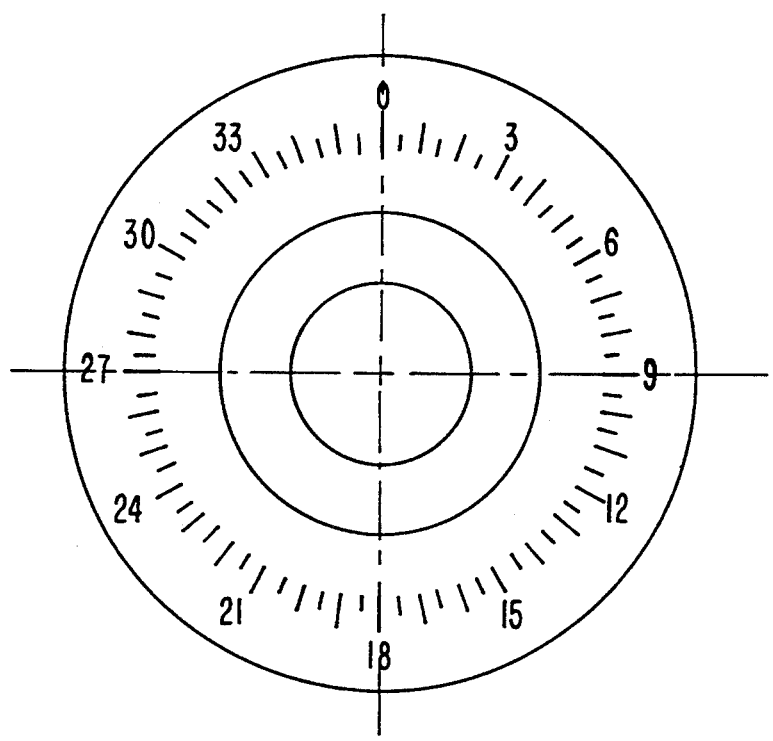
FIG. 14 is a top view of the markings shown on the top of the spindle of FIG. 13.
Figure 15:
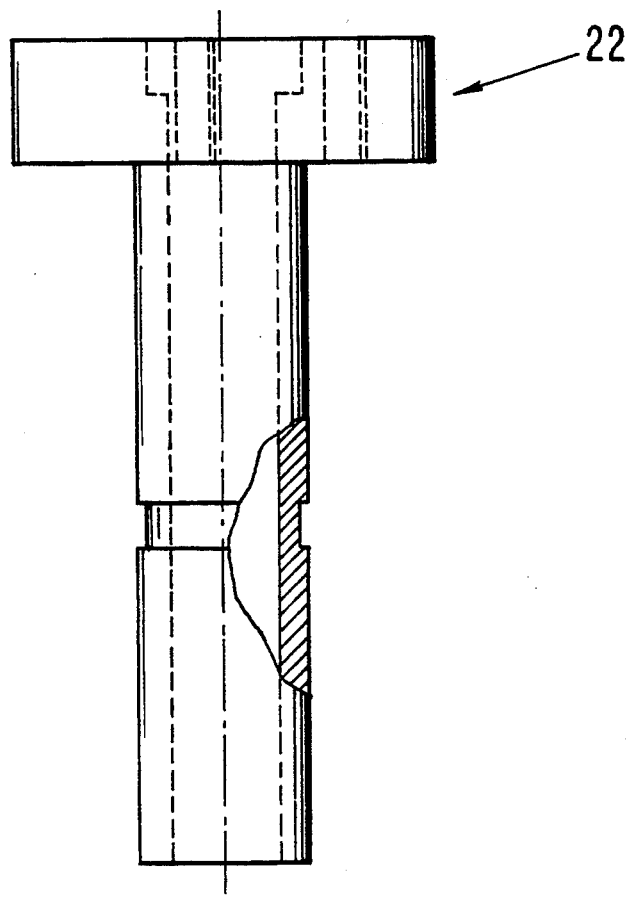
FIG. 15 is a side plan view of the shaft of FIG. 7.
Figure 16:
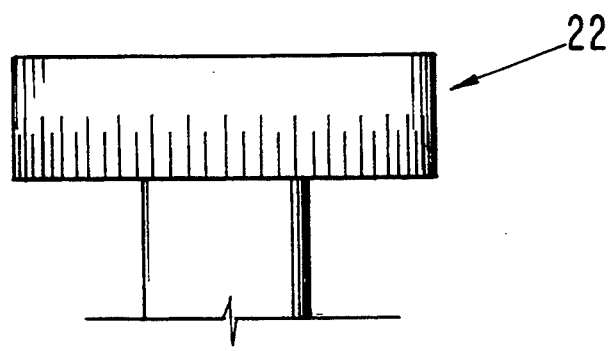
FIG. 16 is a side view of the shaft of FIG. 7 showing markings.

FIGS. 11 and 12 show side views of the spindle 30, FIG. 13 shows a top view of the spindle 30, FIG. 15 shows a side view of the central shaft 22, and FIG. 17 shows a top view of the central shaft 22 of the preferred embodiment of the invention (also see FIGS. 8 and 9). The spindle 30 is rotatably disposed within the central shaft 22 (see FIG. 9). The horizontal wings 18 and 26 (see top view in FIG. 19) are rotatably disposed around the spindle 30 (see FIG. 9). Markings, preferably showing a 360° rotation, are present on the top of the spindle 30, as shown in a detailed top view of the spindle in FIG. 14. Likewise, markings may be present on the side of the central shaft 22, such as shown in FIG. 16, and on the horizontal side wings 18 and 26, such as shown in FIG. 19.

FIG. 18 shows a top view of the central mount 47. As shown therein, a circular plate 53 has six holes 51,55 unequally spaced such that three holes 55 can be aligned and regularly realigned in the same position to sit atop the shaft 22 (also see FIG. 17); thus the plate 53 is always put on the same way. The additional three holes 51 (see FIG. 18) carry hexhead screws which push the plate 53 away from the mounting face while the other three holes 55 carry hexhead screws which pull the plate 53 toward the mounting surface. This push/pull arrangement provides for greater calibration. By varying the tension in the screws the angle of the plate 53 to the central axis of the bore of the shaft can be changed and thereby change the angle of the central laser light and allowing for easy calibration of its trajectory. The mounting plate 53 also has a D-shaped hole 57 in the center in which the laser light is directly mounted, thus preventing rotation of the light once it is fixed in place.

Figure 20:
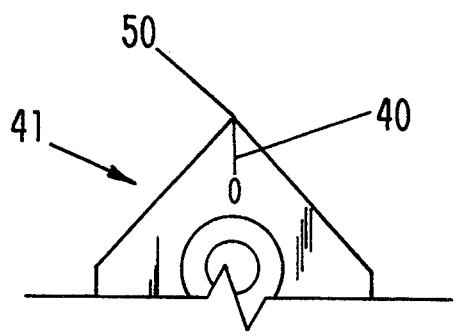
FIG. 20 is a front view of one of the pointers of the focusing lens assembly bracket of FIG. 7, showing a marking.
Figure 23:
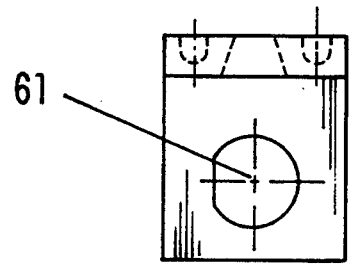
FIG. 23 is a top view of the focusing lens assembly bracket shown in FIG. 21.
Figure 24:
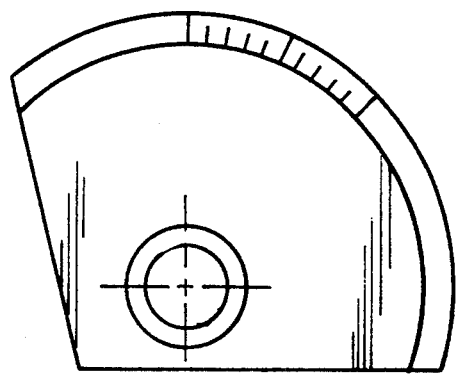
FIG. 24 is a front view of one of the vertical azimuth bezels of FIG. 7, showing markings.
Figure 25:
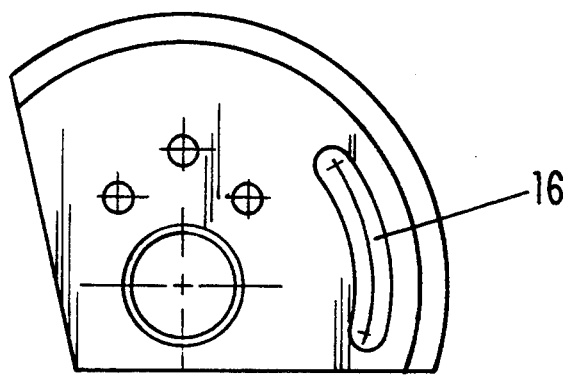
FIG. 25 is a front view of one of the vertical azimuth bezels of FIG. 7.
Figure 26:
FIG. 26 is a side view of the vertical azimuth bezel of FIG. 25.
Figure 27:
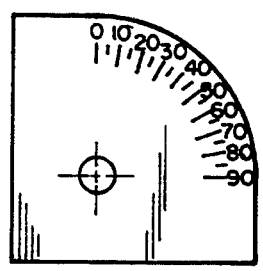
FIG. 27 is a front view of one of the horizontal bezel carriages of FIG. 7, showing markings.

More detailed drawings of some of the side light source mounting and calibration members shown in FIG. 10 are shown in FIGS. 20–30. The pointer 41 of the focusing lens assembly bracket 40 may have a vertical line 48 at the apex 50, as shown in FIG. 20. Likewise, the vertical azimuth bezel 36 may have Vernier scale markings, such as shown in FIG. 24. Similarly, the horizontal bezel carriage 34 may have Vernier scale markings, such as shown in FIG. 27. All of these markings, including the markings on the spindle 30, the central shaft 22 and the side horizontal wings 18 and 26, assist the surgeon or health practitioner to accurately take measurements and thereby determine the location and volume of the tumor or lesion.

Figure 21:
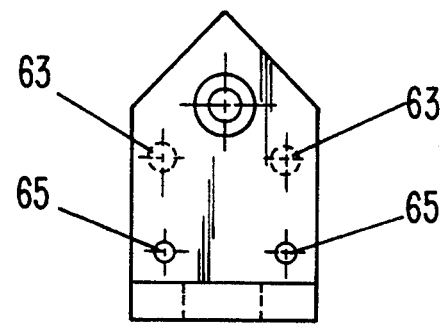
FIG. 21 is a front view of one of the focusing lens assembly brackets of FIG. 7.
Figure 22:
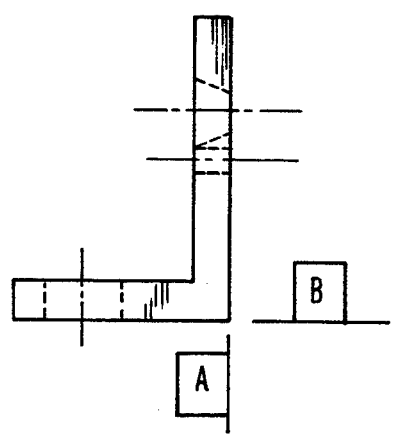
FIG. 22 is a side view of the focusing lens assembly bracket shown in FIG. 21.

The focusing lens bracket assembly 40 has a D-shaped hole 61 disposed at its center, such as shown in FIG. 23, which is used for mounting the lateral light sources. As shown in FIGS. 21 (front view) and 22 (side view), small hexhead set screws 63,65, which push and pull the focusing lens bracket assembly 40, respectively, relative to the vertical azimuth bezel 36 provide for enhanced calibration and accuracy of the laser light trajectories when angles are changed.

Figure 28:
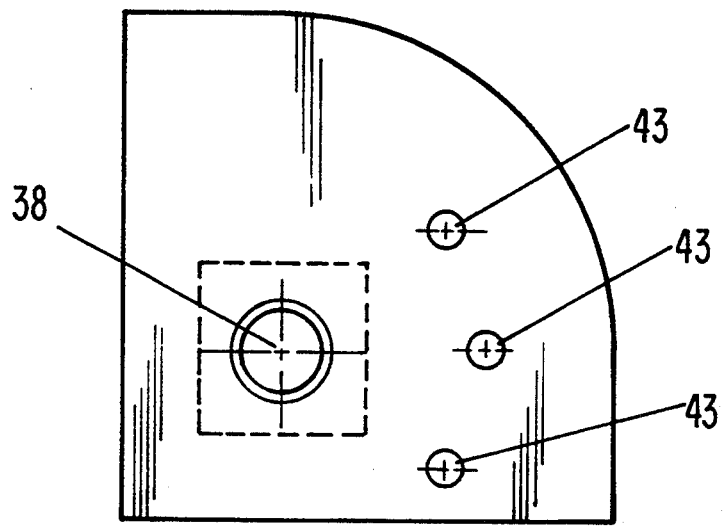
FIG. 28 is a front view of one of the horizontal bezel carriages of FIG. 7.
Figure 29:
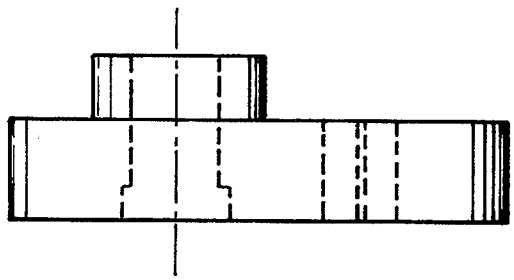
FIG. 29 is a top view of the horizontal bezel carriage of FIG. 28.
Figure 30:
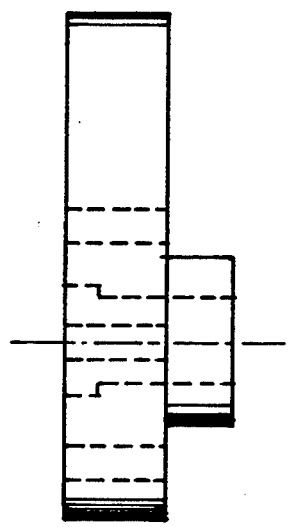
FIG. 30 is a side view of the horizontal bezel carriage of FIG. 28.

Detailed drawings of the vertical azimuth bezel 36 are shown in FIGS. 24–26 and detailed drawings of the horizontal azimuth bezel carriage 34 are shown in FIGS. 27–30. FIG. 25 shows a front view, FIG. 26 shows a side view, and FIG. 24 shows the markings on a front view, of the vertical azimuth bezel 36. FIG. 27 shows the markings on a front view, FIG. 28 shows a front view, FIG. 29 shows a top view, and FIG. 30 shows a side view of the horizontal bezel carriage 34. Set screws 43 disposed on the horizontal azimuth bezel carriage 34, as shown in FIG. 28, are disposed in circular sectional slot 46 disposed in the vertical azimuth bezel 36, as shown in FIG. 25. When the central screw 38 of the horizontal bezel carriage 34 is tightened, it compresses the components of the horizontal bezel carriage 34 together and prevents their canting in relationship to each other.

Figure 31:
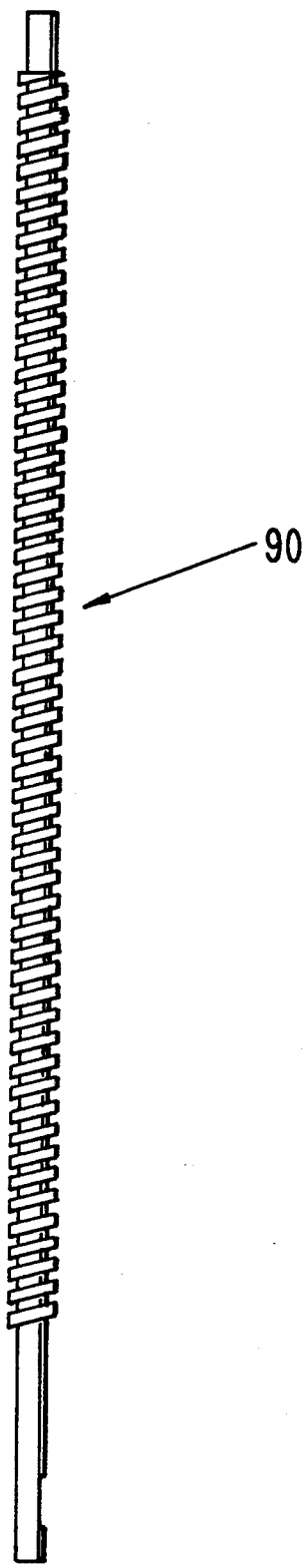
FIG. 31 is an alternative embodiment of the invention showing a worm gear used for adjustments along the horizontal wings.

In an alternative embodiment, such as shown in FIG. 31, the adjustment of side light sources 14 and 16 is accomplished by use of a worm gear 90 which is attached to the horizontal wings 18 and 26 and side light sources 14 and 16. As can be appreciated by those skilled in the art, other means of moving side light sources 14 and 16, may be utilized in accordance with the invention, and the invention is not limited to the embodiments shown in the drawings.

Figure 32:
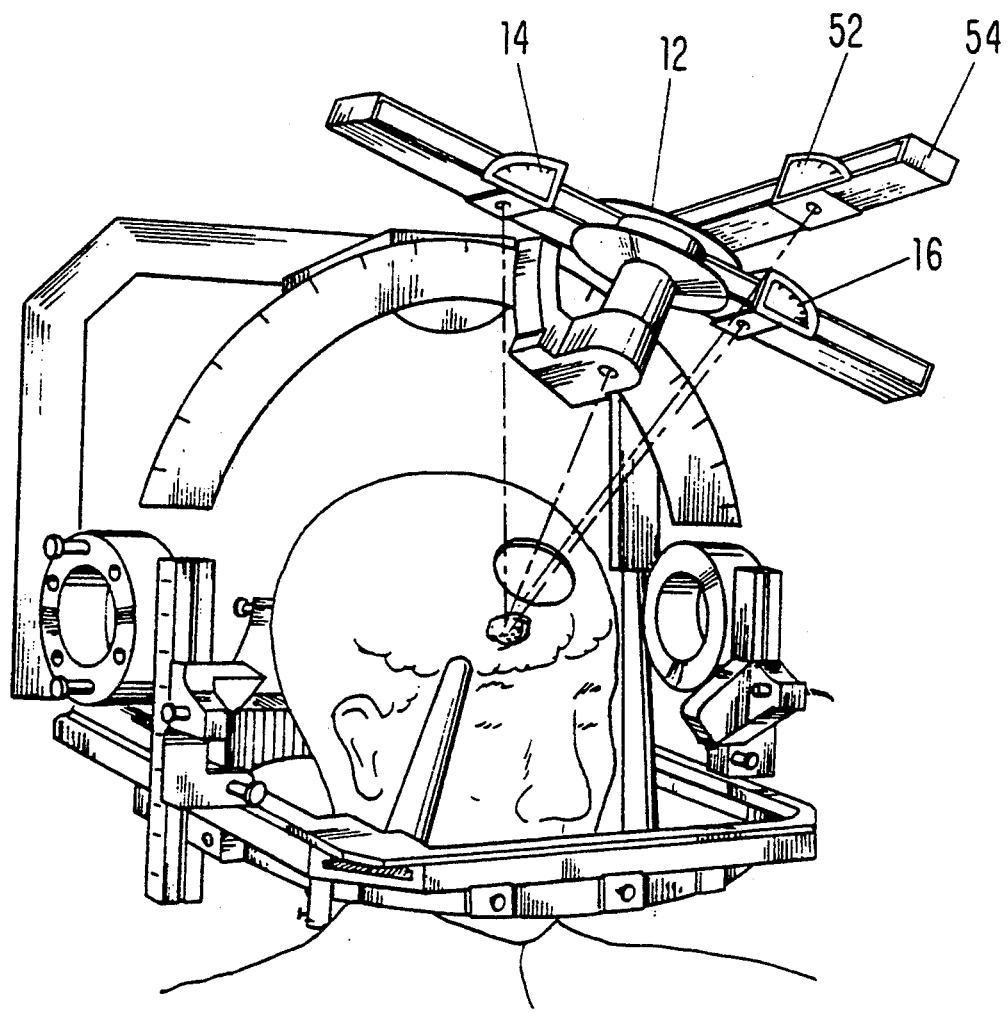
FIG. 32 is a perspective view of an alternative laser localization apparatus of the present invention showing a fixed centrally disposed light source and three additional light sources.

FIG. 32 illustrates an alternative embodiment of the invention, wherein there are three "side" light sources 14, 16, and 52, in addition to the centrally disposed light source 12. All of the discussion above pertains to this alternative embodiment, except there is an additional wing 54 which comprises the third side light source 52. The additional light source 52 enables the practitioner to make even more accurate determinations and measurements. As can be appreciated by those skilled in the art, the invention is not limited to three or four spaced light sources, but may comprise as many light sources as the practitioner may desire to make accurate determinations and measurements.

Figure 33:
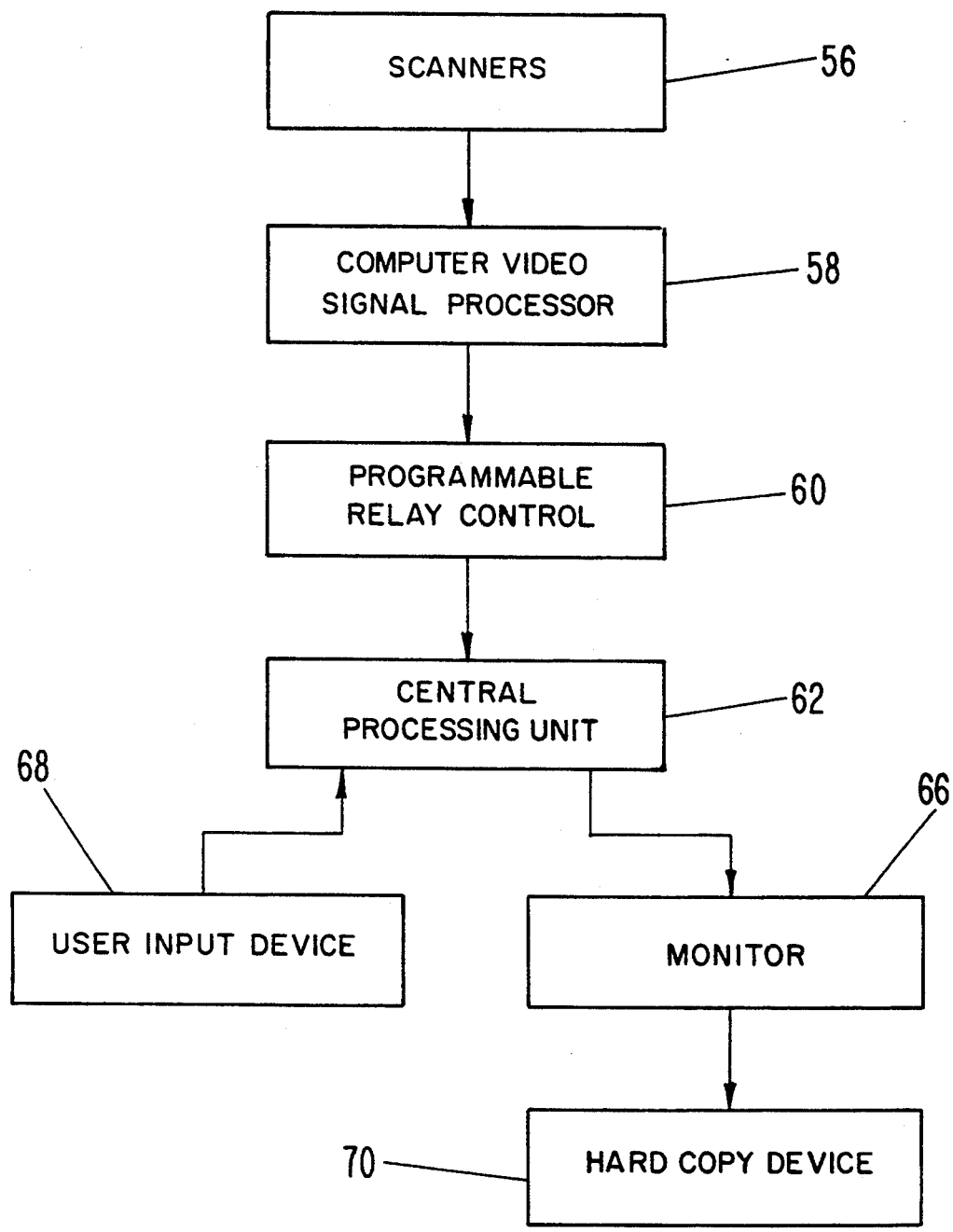
FIG. 33 illustrates a preferred hardware block diagram in accordance with the invention.
Figure 34:
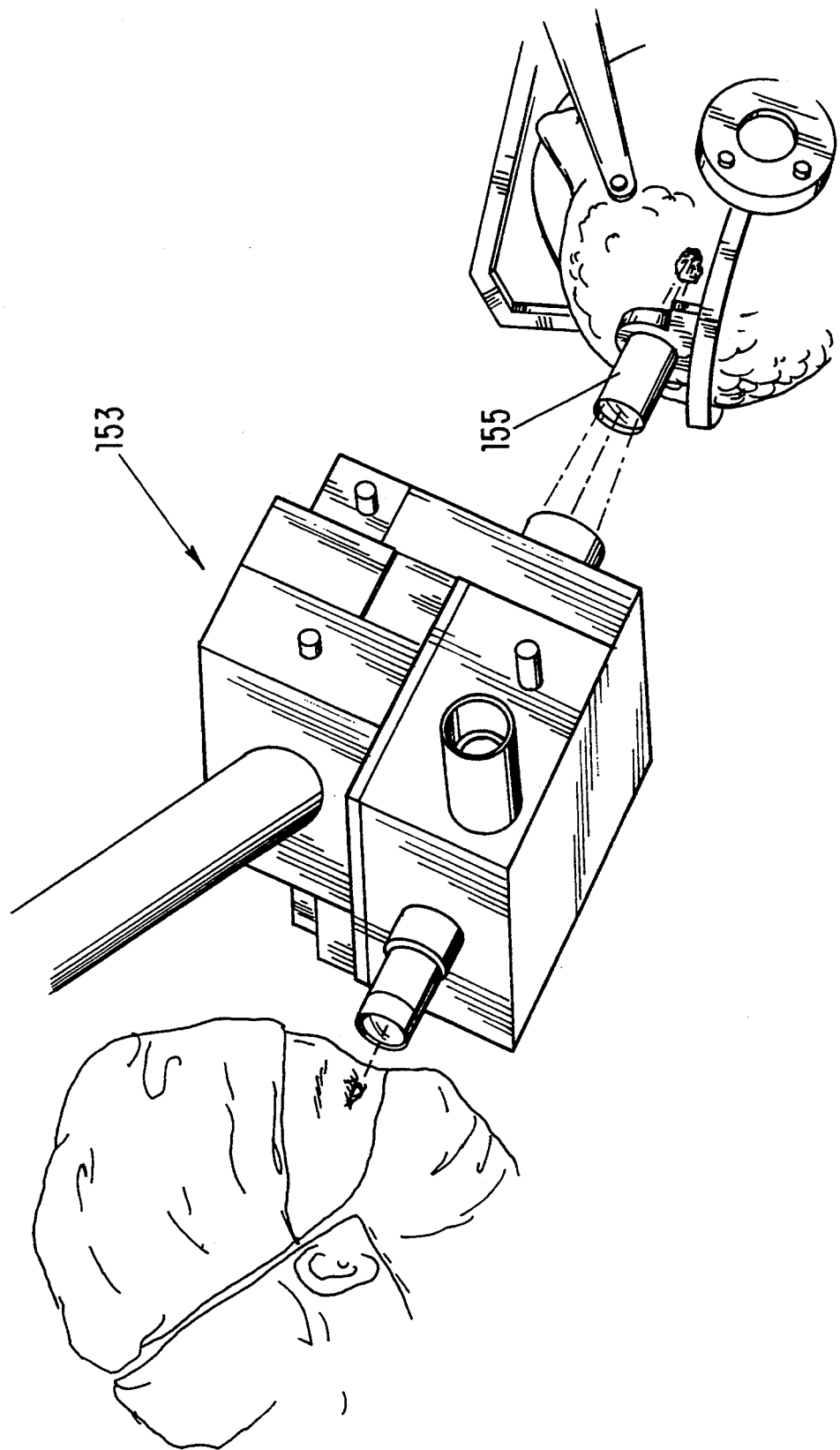
FIG. 34 is an alternative microscope embodiment of the invention.

FIG. 33 illustrates a preferred hardware block diagram in accordance with the invention. Scanners 56, such as CT, magnetic resonance imaging (MRI), PET, DSA, X-ray and various isotope scanners, are provided to obtain various scanning data. This scanning data, which is in various, typically non-standard formats, is convertible to a standard format in accordance with the invention using a PROM computer video signal processor 58. Standard formats which can be used include, but are not limited to, RS-170, CCIR 625 I, RS-343, RS-422, and NTSC. The scanning data may be provided to the computer video signal processor 58 from the scanners 56 by, for example, a BNC connector. The converted scanning data are made available, through programmable relay control 60, to a central processing unit (CPU) 62, such as a 68020/030 VME BUS based CPU with a clock speed up to 30 MHz, preferably comprising hard disk storage, floppy disk storage, streamer tape storage, and a high-resolution frame grabber with a high speed graphics and video image processor. The programmable relay control 60 sets the scanner converter input/output parameters to acquire and convert scanner image data from their various formats to a standard format, for use by the system in accordance with the invention. Alternatively, a scanner converter automatically senses signal input and sets parameters for conversion to a standard format, without the use of user-selectable switches. A user input device 68, such as a high-resolution infrared touch screen and a monitor 66, both connected to the CPU 62, enable the user to selectively manipulate and display the image data. The monitor 66 is preferably a high-resolution color graphics monitor with video inputs for red, green, blue, and composite video signals. The monitor 66 can be configured to operate in either interlaced or non-interlaced mode. Copies of images on the monitor can be provided using a hard copy device 70, such as a high-resolution color videocopy unit.

Software, provided in the CPU 62, is preferably structured on a multi-modular bi-divisional foundation, which comprises a division for image acquisition, enhancement, and manipulation and a division for graphics and user-specific functions. The division for image acquisition, enhancement, and manipulation includes modular software subroutines for: 1) image capture, storage, and achieving; 2) pixel analysis for an entire image or user-defined areas of interest; 3) zoom and pan functions; 4) contrasting and filtering images with functions for smoothing, sharpening, and pseudocoloring; 5) image comparisons; 6) image editing; and 7) various edge detection routines, including Laplacian, Roberts, Sorbel, and Frei routines. The graphics and user-specific functions comprise software modular subroutines that control: 1) the manipulation and swapping of diencephalic and brain-stem atlas maps (preferably at least 117 of such maps) in frontal, sagittal, and horizontal sections; 2) the graphic simulation and the manipulation of various probes and electrodes; 3) alphanumeric functions for demographic data and for coding, storing, and selectively displaying the position of various electrophysiological response points on an electrophysiological map system which preferably comprises at least 2500 electrophysiological response points; 4) measurement functions for determining stereotactic coordinates and other user-specific calculations; and 5) volumetric determinations and two- or three-dimensional simulations.

In yet another alternative embodiment, as shown in FIGS. 34-37, the three-dimensional laser localization apparatus for stereotactic surgery is attached to and incorporated within the optics of a surgical dissecting microscope 153. This embodiment requires that the microscope objective lens 155 be attached to the arc carrier of the stereotactic surgical frame. This embodiment allows for smaller openings, such as for cranial and cerebral openings, for surgical approach to deep-seated intracranial or intracerebral structures and/or lesions.

In this embodiment, the laser light sources are delivered by an optical prismatic system designed such that the primary laser light source is split into at least three separate laser light beams (shown by dashed lines) which project from the microscope's objective lens 155. The prismatic system is designed such that by micrometer and/or digital adjustments the additional (preferably at least two) laser light sources are movable around at an angle in relation to the central laser light beam.

Figure 35:
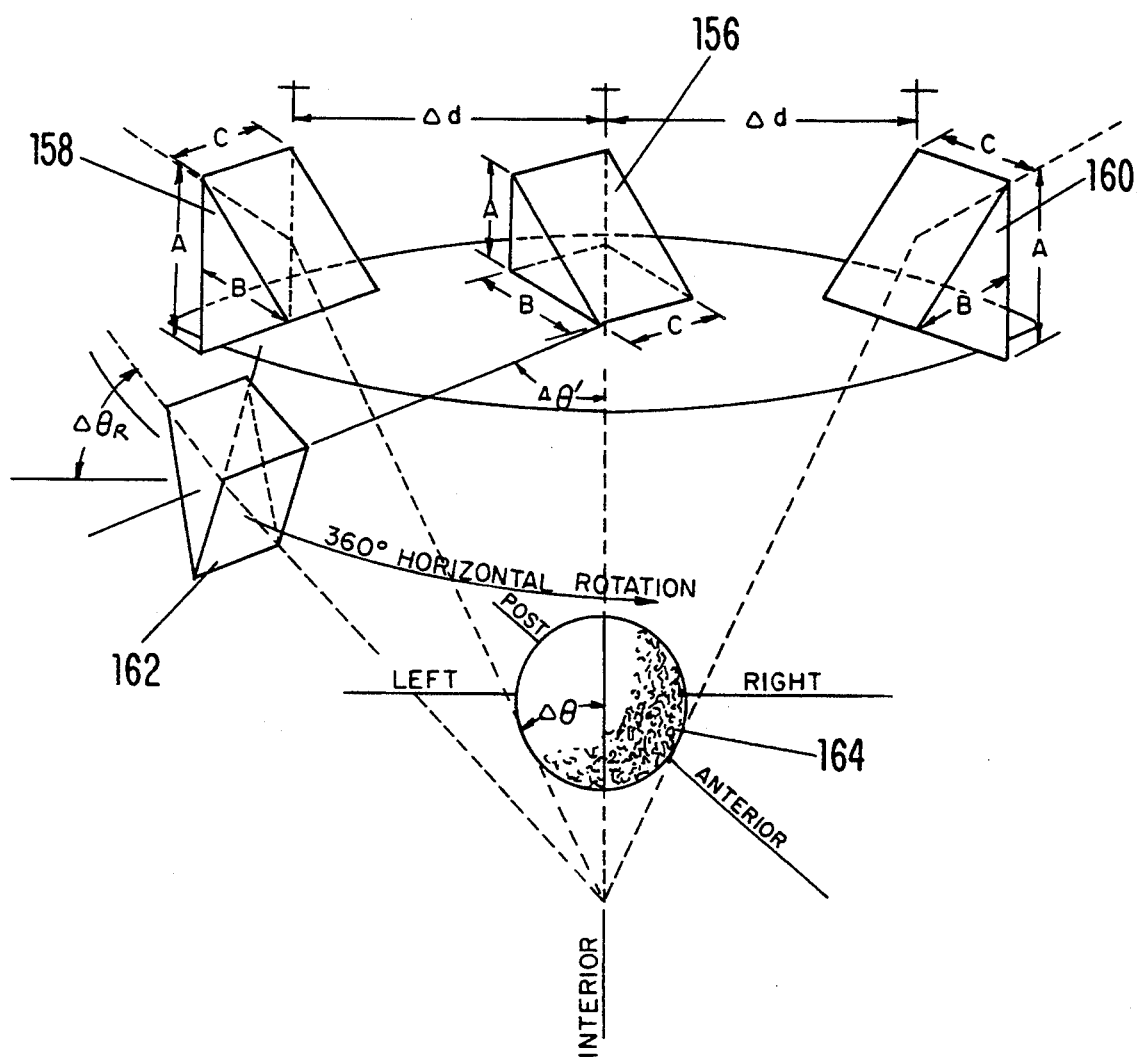
FIGS. 35-37 are diagrams of the light source and prism operation within the microscope embodiment of FIG. 34.
Figure 36:
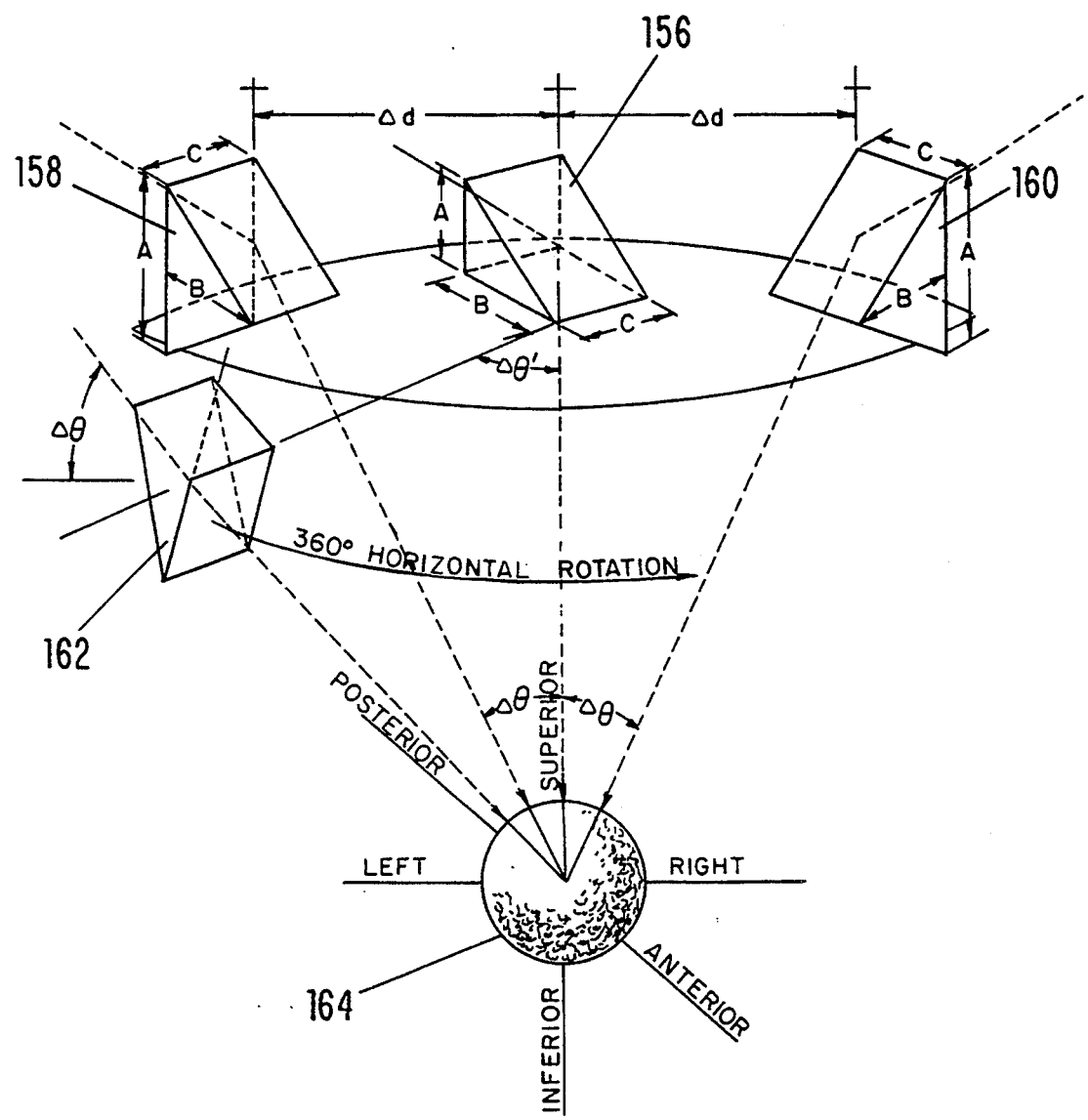
Figure 37:
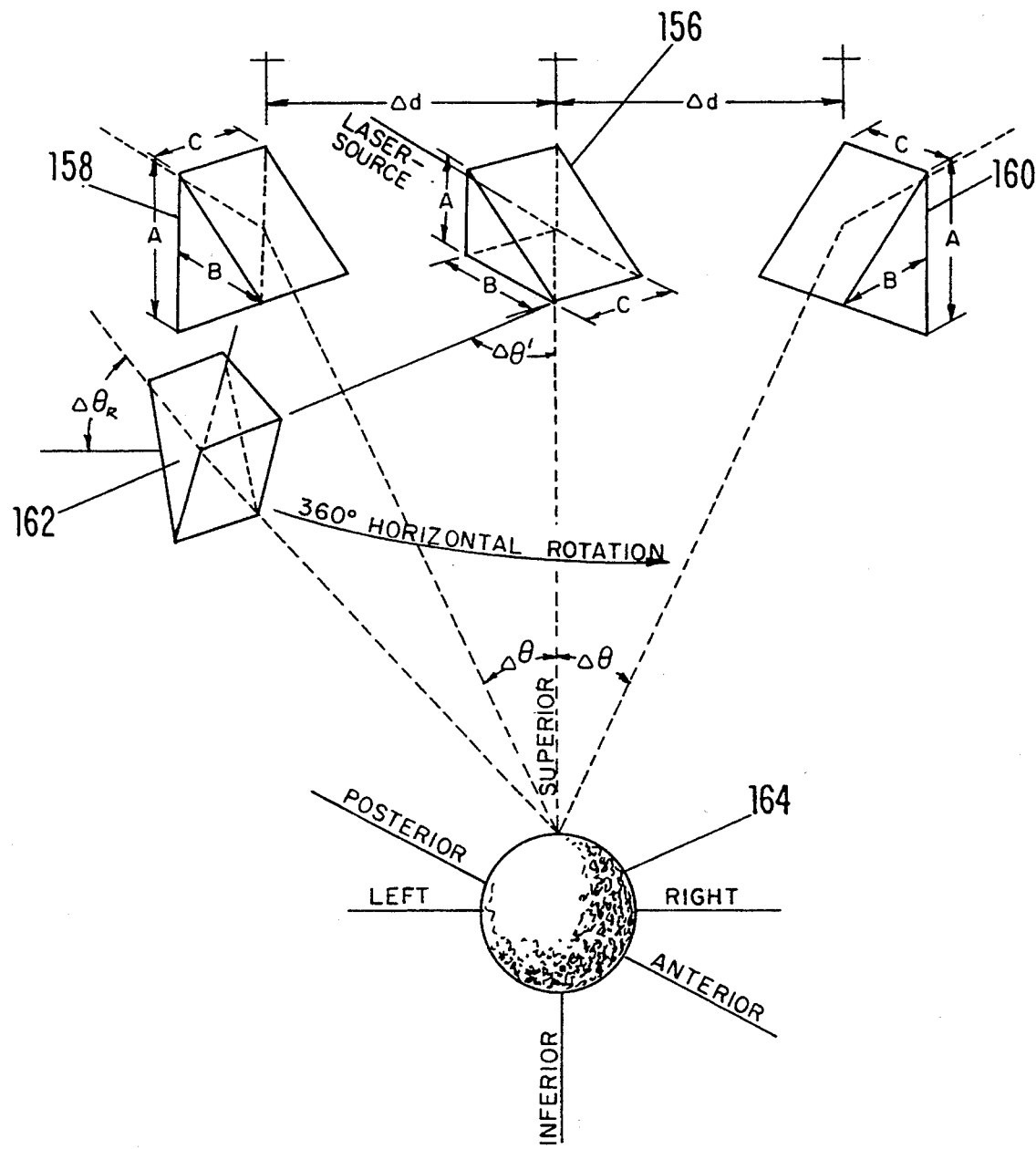

FIGS. 35-37 schematically show the relationships, in this alternative embodiment, among a fixed position light source 156; a first additional variable light source 158, preferably with micrometer or digital adjustment along axes A, B, and C; a second additional variable light source 160, preferably with micrometer or digital adjustment along axes A, B, and C; a rotation prism. 162; and a hypothetical tumor 164. FIGS. 35-37 illustrate the localization of the sides, center and top of the tumor 164, respectively, by the angular rotation of the prism 162 (preferably 360'), the angles between the laser beams, shown as "$\Delta\Theta$", "$\Delta\Theta'$", and "$\Delta\Theta_R$", and the distance between the light sources on the microscope objective mount, shown as "$\mp\Delta d$" in these figures. As can be appreciated by those skilled in the art, this microscope embodiment may comprise more than two additional variable light sources, such as discussed with reference to the preferred embodiment.

Figure 38:
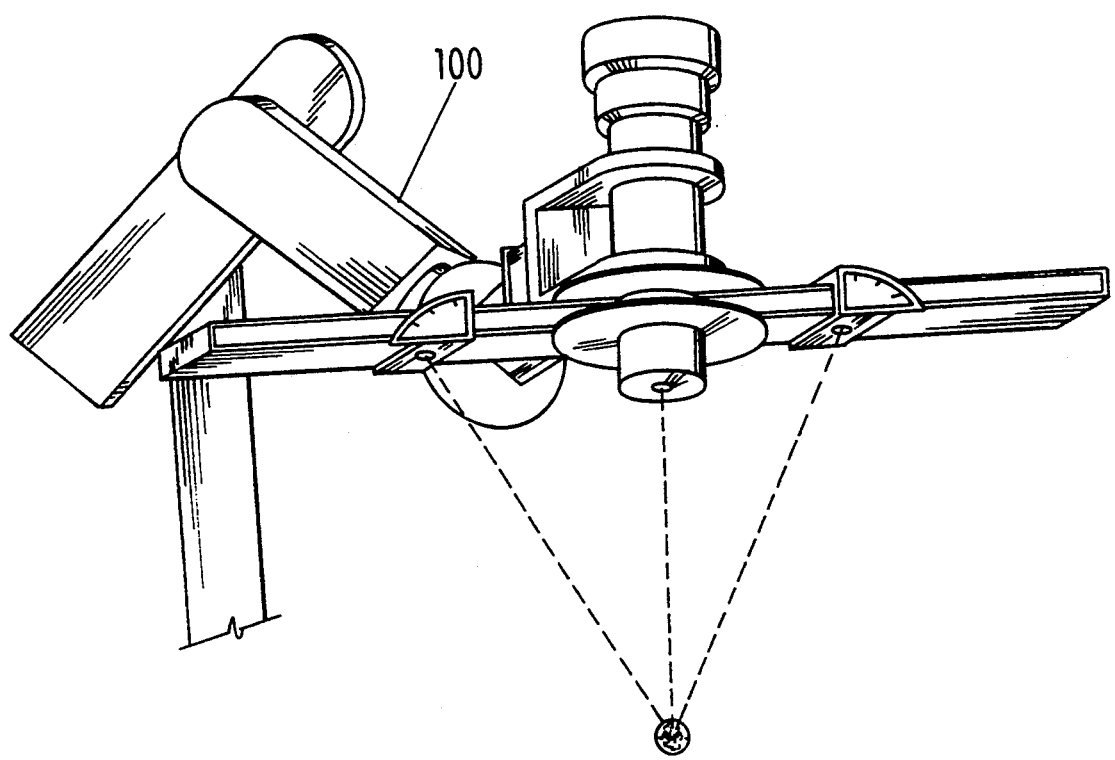
FIG. 38 is an alternative embodiment of the beam localization apparatus of the invention which incorporates an articulating robotic type arm.
Figure 39:
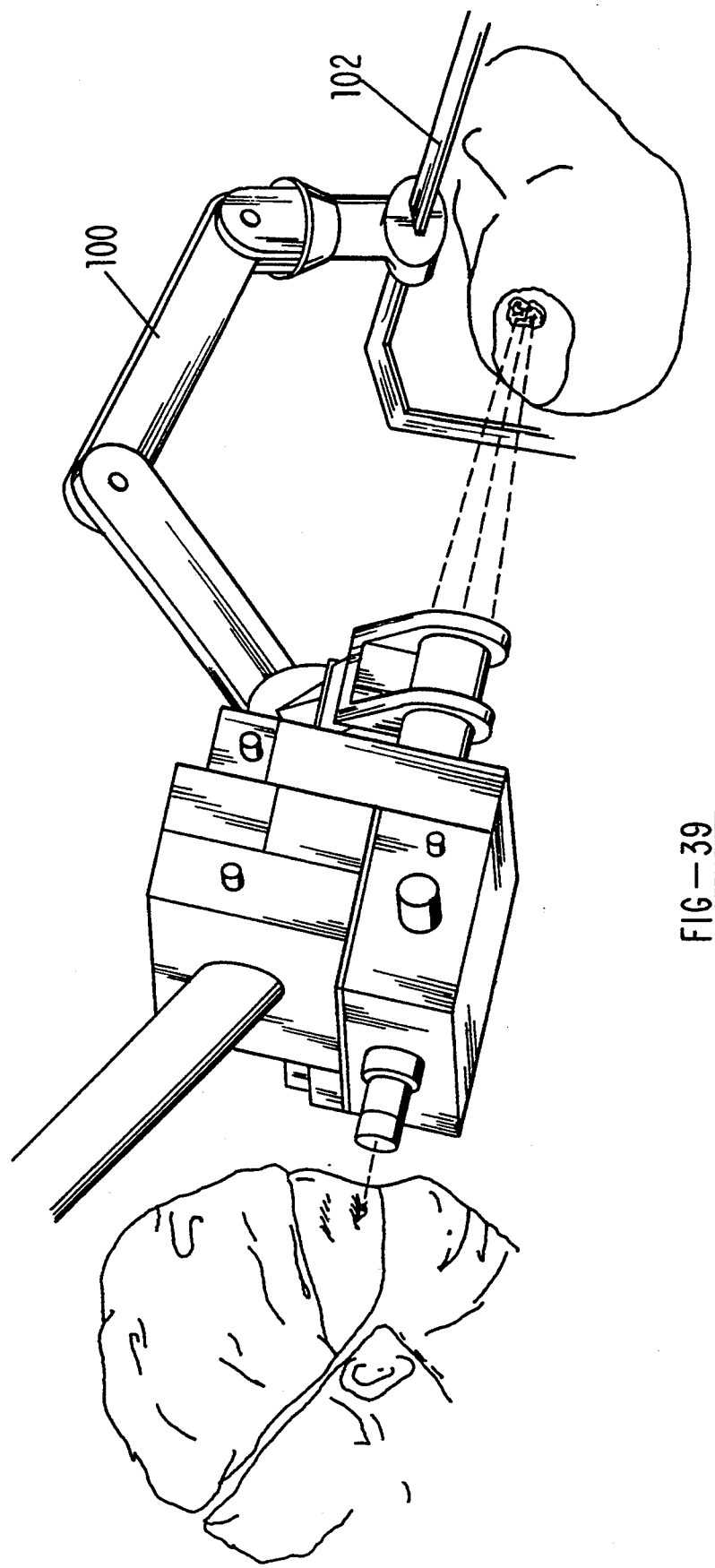
FIG. 39 is an alternative embodiment of the microscope embodiment of the invention which incorporates an articulating robotic type arm attached to the base ring of a stereotactic frame apparatus.

In an additional alternative embodiment, the three-dimensional beam localization apparatus, as shown in FIG. 38, or the microscope embodiment, as shown in FIG. 39, can be attached to an articulating robotic type arm 100. This embodiment allows attachment to any component of a stereotactic localization system, such as a surgical headrest/bodyrest fixation system, the operating room table, or the base ring of a stereotactic apparatus 102, as shown in FIG. 39, and therefore allows a greater range of motion than may be possible with other embodiments of the invention. The purpose of the robotic arm is to provide means for spatial referencing and positioning. Alternatively, infrared or ultrasonic sensing and emitting devices may be employed to spatially locate and assist positioning of the microscope or beam localization embodiment in stereotactic space. This would obviate the need for a robotic arm, or could be used in conjunction with a robotic arm.

The preferred light source, in accordance with the present invention, is a laser light source. The light beams can be transmitted by means common to the art, preferably by either one of two fashions. The laser may be connected by special optic coupling to fine fiber-optic cabling to which a lens system is attached to the associated fiber-optic cabling for projecting the laser light beam. One such fiber-optic laser light linkage for each laser light source is attached to the laser light carrier on the stereotactic frame system. Or, the primary source of all laser light may be from miniaturized laser diodes having the laser light source and lens system incorporated into the laser diodes for projection of the laser light. These sources are connected by special coupling to the laser light carrier on the stereotactic frame system. Each laser diode has connected to it an associated electrical power supply cabling.

The preferred laser light sources, useful in accordance with the invention, are helium-neon lasers, although other suitable laser systems known in the art could also be utilized. In particular, other laser systems should be selected depending on what techniques are to be performed, for instance whether the surgeon or health practitioner is to perform diagnostic techniques or surgical techniques. Too, the light sources can be of the same or different colors or wavelengths to provide for ease of use and accuracy.

Although light sources are discussed above in reference to the embodiments shown in the drawings, other beam or ray sources may be utilized in accordance with the invention. Likewise, the apparatuses shown in the drawings can be accommodated for other types of beam or ray sources.

The invention further comprises a method of determining desired information about a volumetric entity in a body. This method comprises the following steps:

a) positioning a plurality of beam sources on an apparatus fittable on the body;

b) adjusting the spacing and the rotational positions of the beam sources relative to one another so that the beams emitted therefrom intersect at a point on the volumetric entity of the body; and c) using proportional angulation, determining positional information about the entity.

Steps b) and c) may be repeated a multiplicity of times to a series of points on an area or volume of the volumetric entity to determine positional, area, and volumetric information about the volumetric entity.

The stereotactic computer simulation and graphics techniques which may accompany the use of this invention are not discussed herein, however, computer simulation and graphics techniques, common to the art, and the method and apparatus of co-pending patent application Ser. No. 07/290,316, are useful in practicing the invention for providing precise measurements, and interactive user-friendly feedback to the health practitioner.

The invention has been described in detail with particular reference to a preferred embodiments thereof, but it will be understood that variations and modifications can be effected within the scope of the invention.

What is claimed is:

1. A surgical beam localization and surgical microscope apparatus, the apparatus comprising:
    a surgical reference device defining a three-dimensional space;
    a surgical microscope;
    objective lens means disposed on said surgical microscope positioned within said three-dimensional space;
    beam emitting means comprising laser means for emitting at least two beams from two separate and spaced points;
    means for movably adjusting relative positions of said beam emitting points with respect to one another;
    means for aiming said beams at user selected locations on a selected volumetric entity of a body; and
    means for ascertaining desired information about the selected volumetric entity of the body mathematically from positions of said beam emitting means in said apparatus, relative positions to one another of said beam emitting means, and aiming directions of said beams from said beam emitting points.

2. The invention of claim 1 wherein said aiming means comprises robotic arm means.

3. The invention of claim 2 wherein said robotic arm means comprises articulated robotic arm means.

4. The invention of claim 1 wherein said beam emitting means direct said at least two beams through said objective lens means.

5. The invention of claim 1 wherein said beam emitting means direct said at least two beams of said objective lens means.

6. A surgical beam localization apparatus for use with a reference means defining a three-dimensional space, the beam localization apparatus comprising:
    means for emitting a fixed centrally disposed beam;
    means for emitting at least two additional beams;
    first mounting device means for mounting said means for emitting said fixed centrally disposed beam;
    second mounting device means for mounting said means for emitting said at least two additional beams;
    means for mounting said means for emitting a fixed centrally disposed beam on said first mounting device means;
    means for mounting said means for emitting at least two additional beams spaced from and independent of one another and said means for emitting a fixed centrally disposed beam on said second mounting device means;
    means for locating said first and second mounting device means within said three-dimensional space;
    means for movably adjusting positions of said means for emitting at least two additional beams relative to one another, and to said means for emitting a fixed centrally disposed beam;
    robotic arm means for aiming at least one of said beams at a location of a selected volumetric entity of a body;
    means for variably aiming at least one of said beams at an additional location of the selected volumetric entity of the body; and
    calculation means for ascertaining desired information about the selected volumetric entity of the body from position of said means for emitting a fixed centrally disposed beam and said means for emitting at least two additional beams and aiming directions of said beams.

7. The invention of claim 6 wherein said robotic arm means comprises articulated robotic arm means.

8. A surgical beam localization apparatus for use with a reference means defining a three-dimensional space, the beam localization apparatus comprising:
    means for emitting first and second beams from two separate and spaced points;
    mounting device means for mounting said means for emitting first and second beams;
    means for attaching said means for emitting first and second beams on said mounting device means;
    means for movably adjusting relative positions of said means for emitting first and second beams with respect to one another; and
    calculation means for ascertaining desired information about a selected volumetric entity of a body from a position of the mounting device means in the three-dimensional space, relative positions with respect to each other of said means for emitting first and second beams, and aiming directions of said means for emitting first and second beams.

9. The invention of claim 8 additionally comprising robotic arm means for aiming said beams at user selected locations on the body.

10. The invention of claim 9 wherein said robotic arm means comprises articulated robotic arm means.

11. The invention of claim 8 additionally comprising a surgical microscope disposed on said surgical beam localization apparatus for viewing the selected volumetric entity.

12. The invention of claim 8 wherein said calculation means comprise sensor means for determining the positions of said beams emitting means in the three-dimensional space.

13. The invention of claim 12 wherein said sensor means comprises infrared sensor means.

14. A method of localizing surgical beams for use with a surgical microscope, the method comprising the steps of:
   a) providing surgical reference means defining a three-dimensional space;
   b) positioning objective lens means of the surgical microscope within the three-dimensional space;
   c) emitting at least two beams from two separate and spaced points;
   d) movably adjusting relative positions of the beam emitting points with respect to one another;
   e) aiming said beams at user selected locations on a selected volumetric entity of a body; and
   f) ascertaining desired information about the selected volumetric entity of the body mathematically from positions of the beam emitting points, relative positions with respect to one another of the beam emitting points, and aiming directions of the beams.

15. The invention of claim 14 wherein the step of aiming comprises aiming by robotic arm means.

16. The invention of claim 15 wherein the step of aiming by robotic arm means comprises aiming by articulated robotic arm means.

17. The invention of claim 14 wherein the step of emitting at least two beams comprises directing the at least two beams through the objective lens means.

18. The invention of claim 14 wherein the step of emitting at least two beams comprises directing the at least two beams outside the objective lens means.

19. A method of localizing a surgical beam for use with a reference means defining a three-dimensional space, the method comprising the steps of:
   a) providing means for emitting a fixed centrally disposed beam;
   b) providing means for emitting at least two additional beams;
   c) mounting on a first mounting device the means for emitting the fixed centrally disposed beam;
   d) mounting on a second mounting device the means for emitting the at least two additional beams;
   e) locating the first and second mounting devices within the three-dimensional space;
   f) movably adjusting the positions of the means for emitting at least two additional beams relative to one another, and to the means for emitting a fixed centrally disposed beam;
   g) aiming by robotic arm means at least one of the beam emitting means at a location of a selected volumetric entity of a body;
   h) variably aiming at leas tone of the beam emitting means at an additional location of the selected volumetric entity of the body; and
   i) ascertaining desired information about the selected volumetric entity of the body from positions of the means for emitting a fixed centrally disposed beam and the means for emitting at least two additional beams and aiming directions of said beam emitting means.

20. The invention of claim 19 wherein the aiming by robotic arm means step comprises aiming by articulated robotic arm means.

21. A method of a localizing surgical beam for use with a reference means defining a three-dimensional space, the method comprising the step of:
   a) providing means for emitting first and second beams from two separate and spaced points;
   b) mounting on a mounting device the means for emitting first and second beams;
   c) movably adjusting the relative positions of the means for emitting first and second beams with respect to one another; and
   d) ascertaining desired information about a selected volumetric entity of a body from a position of the mounting device in the three-dimensional space, relative positions with respect to each other of the means for emitting first and second beams, and aiming directions of the means for emitting first and second beams.

22. The invention of claim 21 additionally comprising the step of aiming the first beam at a user selected location on the body.

23. The invention of claim 22 wherein the aiming step comprises aiming by robotic arm means.

24. The invention of claim 23 wherein the step of aiming by robotic arm means comprises aiming by articulated robotic arm means.

25. The invention of claim 21 additionally comprising the step of viewing the selected volumetric entity through a surgical microscope.

26. The invention of claim 21 wherein the ascertaining step comprises determining by sensor means the positions of the beam emitting means in the three-dimensional space.

27. The invention of claim 26 wherein the determining step comprises determining by infrared sensor means.

* * * * *